US011056225B2

(12) United States Patent
    el Kaliouby et al.

(10) Patent No.: US 11,056,225 B2
(45) Date of Patent: Jul. 6, 2021

(54) ANALYTICS FOR LIVESTREAMING BASED ON IMAGE ANALYSIS WITHIN A SHARED DIGITAL ENVIRONMENT

(71) Applicant: Affectiva, Inc., Boston, MA (US)

(72) Inventors: Rana el Kaliouby, Milton, MA (US); James Henry Deal, Jr., Duvall, WA (US); Forest Jay Handford, Berlin, MA (US); Panu James Turcot, Pacifica, CA (US); Gabriele Zijderveld, Somerville, MA (US)

(73) Assignee: Affectiva, Inc., Boston, MA (US)

( * ) Notice: Subject to any disclaimer, the term of this patent is extended or adjusted under 35 U.S.C. 154(b) by 189 days.

(21) Appl. No.: 15/444,544

(22) Filed: Feb. 28, 2017

(65) Prior Publication Data

US 2017/0171614 A1    Jun. 15, 2017

Related U.S. Application Data

(63) Continuation-in-part of application No. 15/262,197, filed on Sep. 12, 2016, now abandoned, which is a
(Continued)

(51) Int. Cl.
    *A63F 13/86*    (2014.01)
    *A61B 5/16*    (2006.01)
    (Continued)

(52) U.S. Cl.
    CPC .......... *G16H 20/70* (2018.01); *A61B 5/0077* (2013.01); *A61B 5/165* (2013.01); *A61B 5/7264* (2013.01);
    (Continued)

(58) Field of Classification Search
    None
    See application file for complete search history.

(56) References Cited

U.S. PATENT DOCUMENTS 3,034,500 A    5/1962    Backster, Jr.
3,548,806 A    12/1970    Fisher
(Continued)

FOREIGN PATENT DOCUMENTS

| JP | 08115367 | 7/1996 |
|----|----------|--------|
| KR | 10-2005-0021759 A | 3/2005 |
| KR | 10-2008-0016303 A | 2/2008 |
| KR | 1020100048688 A | 5/2010 |
| WO | WO 2011/045422 A1 | 4/2011 |

OTHER PUBLICATIONS

Albiol, Alberto, et al. "Face recognition using HOG-EBGM." Pattern Recognition Letters 29.10 (2008): 1537-1543.
(Continued)

*Primary Examiner* — Damon J Pierce
(74) *Attorney, Agent, or Firm* — Adams Intellex, PLC

(57) ABSTRACT

Analytics are used for live streaming based on image analysis within a shared digital environment. A group of images is obtained from a group of participants involved in an interactive digital environment. The interactive digital environment can be a shared digital environment. The interactive digital environment can be a gaming environment. Emotional content within the group of images is analyzed for a set of participants within the group of participants. Results of the analyzing of the emotional content within the group of images are provided to a second set of participants within the group of participants. The analyzing emotional content includes identifying an image of an individual, identifying a face of the individual, determining facial regions, and performing content evaluation based on applying image classifiers.

33 Claims, 21 Drawing Sheets

Related U.S. Application Data continuation-in-part of application No. 14/796,419, filed on Jul. 10, 2015, now abandoned, which is a continuation-in-part of application No. 13/153,745, filed on Jun. 6, 2011, now abandoned, said application No. 14/796,419 is a continuation-in-part of application No. 14/460,915, filed on Aug. 15, 2014, which is a continuation-in-part of application No. 13/153,745, filed on Jun. 6, 2011, now abandoned.

(60) Provisional application No. 62/301,558, filed on Feb. 29, 2016, provisional application No. 62/370,421, filed on Aug. 3, 2016, provisional application No. 62/439,928, filed on Dec. 29, 2016, provisional application No. 62/442,291, filed on Jan. 4, 2017, provisional application No. 62/442,325, filed on Jan. 4, 2017, provisional application No. 62/448,448, filed on Jan. 20, 2017, provisional application No. 62/217,872, filed on Sep. 12, 2015, provisional application No. 62/222,518, filed on Sep. 23, 2015, provisional application No. 62/265,937, filed on Dec. 10, 2015, provisional application No. 62/273,896, filed on Dec. 31, 2015, provisional application No. 62/023,800, filed on Jul. 11, 2014, provisional application No. 62/047,508, filed on Sep. 8, 2014, provisional application No. 62/082,579, filed on Nov. 20, 2014, provisional application No. 62/128,974, filed on Mar. 5, 2015, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014.

(51) Int. Cl.

| | |
|---|---|
| *G06K 9/00* | (2006.01) |
| *G16H 20/70* | (2018.01) |
| *H04N 21/442* | (2011.01) |
| *H04N 21/4223* | (2011.01) |
| *H04N 21/2187* | (2011.01) |
| *H04N 21/478* | (2011.01) |
| *H04N 21/233* | (2011.01) |
| *H04N 21/422* | (2011.01) |
| *A63F 13/213* | (2014.01) |
| *A63F 13/92* | (2014.01) |
| *A63F 13/58* | (2014.01) |
| *G06K 9/46* | (2006.01) |
| *A61B 5/00* | (2006.01) |
| *G06K 9/62* | (2006.01) |
| *G16H 50/70* | (2018.01) |
| *G16H 20/30* | (2018.01) |
| *G16H 50/30* | (2018.01) |
| *G16H 40/67* | (2018.01) |
| *G06Q 30/02* | (2012.01) |

(52) U.S. Cl.
CPC ............ *A63F 13/213* (2014.09); *A63F 13/58* (2014.09); *A63F 13/86* (2014.09); *A63F 13/92* (2014.09); *G06K 9/0053* (2013.01); *G06K 9/00228* (2013.01); *G06K 9/00302* (2013.01); *G06K 9/00335* (2013.01); *G06K 9/00718* (2013.01); *G06K 9/4642* (2013.01); *G06K 9/6218* (2013.01); *G06K 9/6277* (2013.01); *G16H 20/30* (2018.01); *G16H 40/67* (2018.01); *G16H 50/30* (2018.01); *G16H 50/70* (2018.01); *H04N 21/2187* (2013.01); *H04N 21/233* (2013.01); *H04N 21/4223* (2013.01); *H04N 21/42203* (2013.01); *H04N 21/44218* (2013.01); *H04N 21/4781* (2013.01); *H04N 21/47815* (2013.01); *A61B 5/6898* (2013.01); *G06Q 30/0242* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ballet et al. |
| 6,222,607 B1 | 4/2001 | Szajewski et al. |
| 6,309,342 B1 | 10/2001 | Blazey et al. |

(56) References Cited

U.S. PATENT DOCUMENTS

| | | |
|---|---|---|
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1* | 7/2012 | Moon ............... G06Q 30/0201 705/7.29 |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0243930 A1* | 10/2007 | Zalewski ............... G06Q 30/02 463/35 |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0042646 A1* | 2/2009 | Sarkar ................. H04L 67/145 463/29 |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0119730 A1* | 5/2009 | Perlman ................. A63F 13/12 725/114 |
| 2009/0133048 A1 | 5/2009 | Gibbs et al. |
| 2009/0150919 A1 | 6/2009 | Lee et al. |
| 2009/0164132 A1* | 6/2009 | Jung ..................... G16B 45/00 702/19 |
| 2009/0193344 A1 | 7/2009 | Smyers |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0223995 A1* | 9/2011 | Geisner ................. G06F 3/011 463/36 |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2014/0172910 A1 | 6/2014 | Jung et al. |
| 2016/0104486 A1 | 4/2016 | Penilla et al. |
| 2017/0003784 A1* | 1/2017 | Garg ..................... A63F 13/87 |

OTHER PUBLICATIONS

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

(56) References Cited

OTHER PUBLICATIONS

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

\* cited by examiner

ANALYTICS FOR LIVESTREAMING BASED ON IMAGE ANALYSIS WITHIN A SHARED DIGITAL ENVIRONMENT

RELATED APPLICATIONS

This application claims the benefit of U.S. provisional patent application "Analytics for Live Streaming Based on Image Analysis within a Shared Digital Environment" Ser. No. 62/301,558, filed Feb. 29, 2016, "Deep Convolutional Neural Network Analysis of Images for Mental States" Ser. No. 62/370,421, filed Aug. 3, 2016, "Image Analysis Framework Using Remote Learning with Deployable Artifact" Ser. No. 62/439,928, filed Dec. 29, 2016, "Smart Toy Interaction Using Image Analysis" Ser. No. 62/442,291, filed Jan. 4, 2017, "Audio Analysis Learning Using Video Data" Ser. No. 62/442,325, filed Jan. 4, 2017, and "Vehicle Manipulation Using Occupant Image Analysis" Ser. No. 62/448,448, filed Jan. 20, 2017. This application is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015. The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014. The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to image analysis and more particularly to analytics for live streaming based on image analysis within a shared digital environment.

BACKGROUND

Human beings have a wide variety of emotions that can be experienced under certain circumstances. Much work has been done in recent years on detection of human emotions using computer-implemented techniques that rely on image processing of the human face. The facial expressions generated by a human experiencing an emotion are often subconscious, and can convey feelings and sentiments that a person is currently experiencing.

Computerized image analysis is becoming more prevalent in a variety of applications. As computer processing power increases, and the cost of processors and memory decreases, it is becoming possible to perform computerized image analysis in electronic devices available to the typical consumer. One such type of analysis, which includes human facial image analysis, is becoming an increasingly more important technology. Facial image analysis may include aspects such as face detection, face recognition, and face tracking, eye tracking, and so on. Additionally, image capture devices such as cameras have improved in image resolution while simultaneously decreasing in cost over the past several years. This has enabled the acquisition of images of sufficient detail to perform such analysis in consumer electronic devices.

Facial expressions are critical to human communication because they quickly convey large amounts of information among participants in the communication. The human face forms expressions that are based on conscious and unconscious positioning and movement of the many facial muscles. Facial expressions can efficiently convey mental states, emotional states, moods, and so on. They can vary widely from an open and friendly countenance, to a neutral/bored appearance, to a mean, threatening, hostile countenance, etc. Facial muscle positions and movements form the facial content that conveys mood, emotion, and so on. Facial content includes sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, drowsiness, poignancy, mirth, etc. This facial content can be captured and analyzed for a variety of applications including facial recognition, facial identification, among other applications, and can determine a range of human emotions and mental states. The mental states include frustration, ennui, confusion, cognitive overload, skepticism, delight, satisfaction, calmness, stress, and many others.

Various human expressions can be recognized. For example, a smile is one of the most recognized expressions throughout the world. When smiling or laughing, the cheeks are pulled up and out, and the mouth sides are pulled backwards as well as slightly upwards. This slight upper movement pushes the upper eyelids and produces wrinkles around the eyes. Additionally, the mouth appears to get closer to the nose. A smile may indicate happiness. Similarly, a frown can indicate disappointment, frustration, and/or anger. When frowning, the lip corners are pulled downward, and the brows may be furled or lowered over the eyes. Recognizing smiles and frowns can provide an ability to glean mental state information of a person.

Mental or emotional states can play a role in how people interpret external stimuli. Emotions such as happiness, sadness, fear, laughter, relief, angst, worry, anguish, anger, regret, and frustration are often reflected in facial expressions. Thus, the study of facial expressions and their meanings can provide important insight into human behavior.

SUMMARY

A plurality of images is obtained from a plurality of participants involved in an interactive digital environment. The participants can include spectators or players of a game. The plurality of images can be obtained using a variety of image capture devices including cameras. In embodiments, the plurality of images comprises a video. In embodiments, the plurality of images comprises a plurality of videos. In embodiments, the interactive digital environment can include a digital computer game. Emotional content within the plurality of images is analyzed for a set of participants within the plurality of participants. The results of the analyzing of the emotional content within the plurality of images is provided to a second set of participants within the plurality of participants. The analyzing emotional content within the plurality of images includes identifying an image of an individual within the plurality of participants, identifying a face of the individual, determining regions within the face of the individual, and performing an evaluation of content of the face based on applying image classifiers to the regions within the face of the individual. The interactive digital environment can be a shared digital environment for the plurality of participants. The interactive digital environment can include a digital computer game, including a competitive digital computer game. The analyzing can include analyzing spending habits of a third set of participants within the plurality of participants. Results of the analyzing of the emotional content within the plurality of images can be provided to a plurality of viewers of the interactive digital environment. In embodiments, a viewer, from the plurality of viewers, can become a player within the interactive digital environment. The viewer can receive attributes associated with the participant and can assume the role of the player during a playback of the interactive digital environment. In embodiments, a viewer receives attributes associated with the player. Images are obtained from a plurality of viewers of the interactive digital environment. Emotional content is analyzed within the plurality of images for a set of viewers within the plurality of viewers, and results are aggregated of the analyzing the emotional content within the plurality of images for a set of viewers within the plurality of viewers.

A computer-implemented method for analysis is disclosed comprising: obtaining a plurality of images from a plurality of participants involved in an interactive digital environment; analyzing emotional content within the plurality of images for a first set of participants within the plurality of participants; and providing results of the analyzing of the emotional content within the plurality of images to a second set of participants within the plurality of participants. In embodiments, there is provided a computer program product embodied in a non-transitory computer readable medium for analysis, the computer program product comprising code which causes one or more processors to perform operations of: obtaining a plurality of images from a plurality of participants involved in an interactive digital environment; analyzing emotional content within the plurality of images for a first set of participants within the plurality of participants; and providing results of the analyzing of the emotional content within the plurality of images to a second set of participants within the plurality of participants. In some embodiments, a computer system for analysis is provided, comprising: a memory which stores instructions; one or more processors attached to the memory wherein the one or more processors, when executing the instructions which are stored, are configured to: obtain a plurality of images from a plurality of participants involved in an interactive digital environment; analyze emotional content within the plurality of images for a first set of participants within the plurality of participants; and provide results of the analyzing of the emotional content within the plurality of images to a second set of participants within the plurality of participants.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
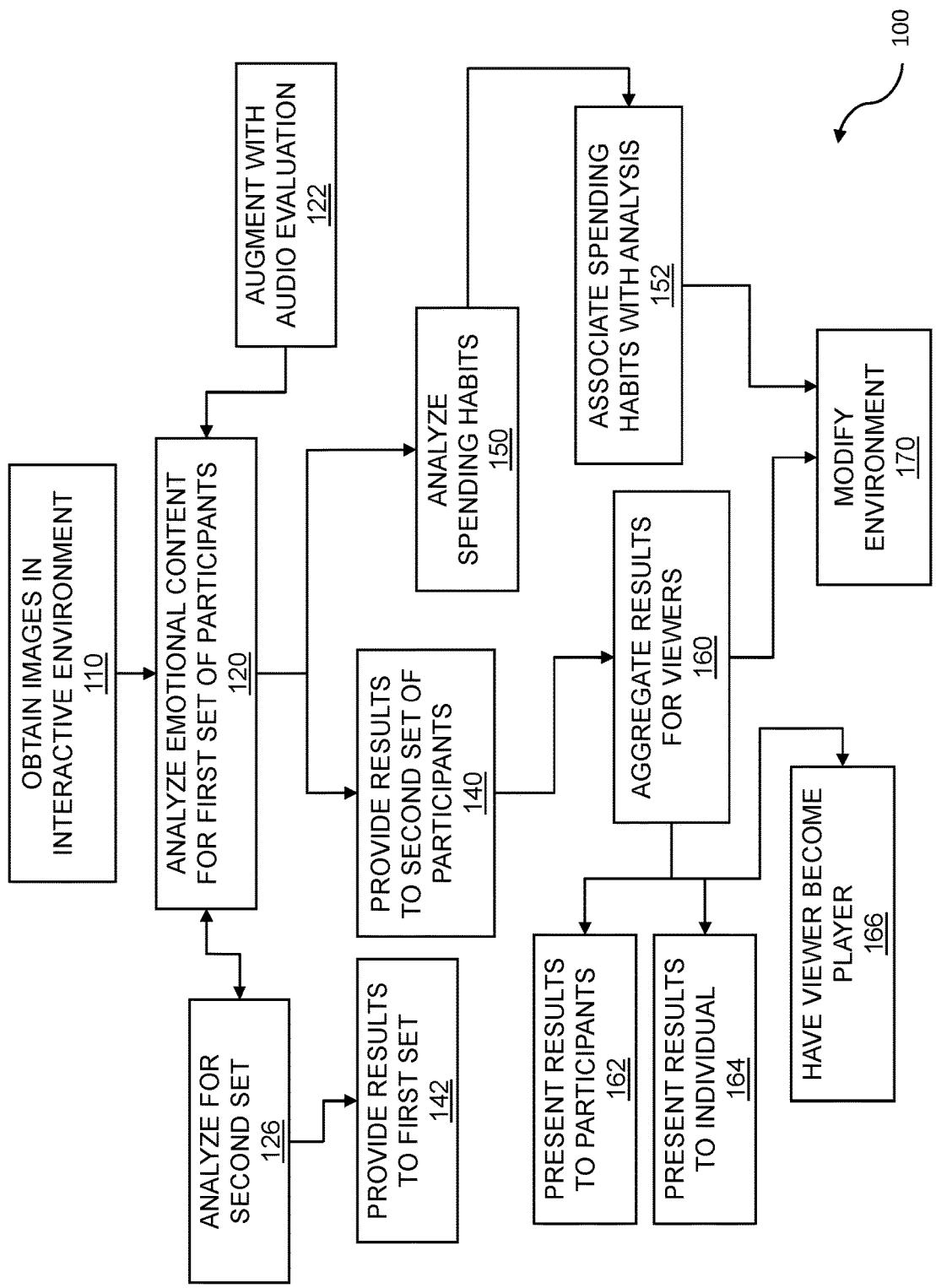
FIG. 1 is a flow diagram for analytics for image analysis within a shared digital environment.

Humans are continuously experiencing their surroundings by using their senses. They observe and process environmental stimuli using sight, hearing, smell, touch, and so on. A large part of human interaction is based on observing one another's faces. As such, sight plays a fundamental role in social interaction. The ability to observe the face of another person during social interaction is critical because the human face is highly expressive. The numerous facial expressions that are exhibited range widely and can convey a person's mental or emotional state, and so on. For example, while a sultry smile communicates one message to the recipient of the smile, an angry frown communicates quite a different one. In another example, a neutral expression can indicate ennui, inattention, indifference, lassitude, and so on. The effective communication of information that is the basis of this social exchange among the participants in the interaction greatly influences how the interaction progresses. A smile may attract people to the interaction and hold their attention, while the angry frown can cause people to leave the interaction, perhaps expediently.

Facial content can communicate significant information among various people participating in an interactive digital environment. In embodiments, the interactive digital environment is a shared digital environment for the plurality of participants. The smile, frown, or neutral expressions mentioned above can be determined in images, videos, etc. The facial content, including facial expressions, can communicate engagement in the interactive digital environment, displeasure or disapproval, boredom, etc. The facial content can be analyzed using a variety of techniques including applying image classifiers, applying image processing algorithms and heuristics, and so on. The content of the face can include analyzing emotional content of the images. The results of the analysis can include detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, drowsiness, poignancy, mirth, and so on. The results of the analysis can be used for a variety of purposes including providing the results to some or all participants in an interactive digital environment. The results of the analysis can be used for editing video footage of an event in an interactive digital environment, for purposes of extracting interesting portions of the video, for creating a "highlights reel" of the video, producing a video that includes emotional data, altering the difficulty of a game within a shared digital environment, and so on. The emotional content identified by the analysis can be used to focus marketing on content that can provide the biggest emotional impact, for pre-populating a post to social media, etc.

In this technique, a plurality of images is obtained from a plurality of participants involved in an interactive digital environment. The images can be captured using a camera or other image capture device, a sensor, etc. The images can be videos, frames of a video, still images, or other image capture media. The emotional content within the plurality of images for a set of participants within the plurality of participants is analyzed. The analyzing emotional content within the plurality of images includes identifying an image of an individual within the plurality of participants; identifying a face of the individual; determining regions within the face of the individual; and performing an evaluation of content of the face based on applying image classifiers to the regions within the face of the individual. Regions within the face of the individual can include eyebrows, eyes, a nose, a mouth, ears, etc. In embodiments, the facial content includes emotional content. The emotional content of the face can include a facial expression. The interactive digital environment can be a shared digital environment for the plurality of participants, and the interactive digital environment can include a competitive digital game. Thus, in embodiments, the interactive digital environment includes a video game. The results of the analyzing of the emotional content within the plurality of images can be provided to a plurality of viewers of the interactive digital environment. In embodiments, a viewer, from the plurality of viewers, can become a player within the interactive digital environment. The viewer receives attributes that can be associated with the participant. The viewer can assume the role of the player during a playback of the interactive digital environment. Assuming the role of the player during a playback can permit the viewer to pick up or continue interaction within the interactive digital environment from the point the game was halted, a checkpoint was set, and so on.

FIG. 1 is a flow diagram for image analysis within a shared digital environment. In embodiments, the shared digital environment includes an interactive gaming environment with multiple participants, in which the participants may include players and/or viewers. The flow 100 includes obtaining images 110 in an interactive digital environment. The obtained images can be images of a plurality of participants involved in a game played in an interactive digital environment. The game can include a multiplayer online game. The interactive digital environment can be a website, an online game, etc. The interactive digital environment can be a social media website. The interactive digital environment can be a shared digital environment for the plurality of participants. Participants in the shared digital environment can share digital content, can view digital content, can exchange digital content, and so on. The interactive digital environment can include a digital game. The digital game can be accessible through a website, a game console, a computer, a personal digital device, and so on. The interactive digital environment can include a competitive digital game. The interactive digital environment can include a digital game in which two or more players can participate.

In addition to the participants, others can view the players as they engage in the digital game.

Regarding the obtained images, the image of the individual (participant) can be captured with a camera, where the camera can be any of a variety of cameras. A camera can include a webcam, a video camera, a still camera, a thermal imager, a CCD device, a smartphone camera, a three-dimensional camera, a depth camera, a light field camera, a plenoptic camera, multiple webcams used to show views of a person from different angles, or any other type of image capture apparatus that can allow captured data to be used in an electronic system. The image can be a still image, a frame from a video, a video, and so on. The image can be one image from a series of images of the individual. The series of images can include a video of the individual. The plurality of images can include a video, a series of images, a video clip, live-streamed video, and so on. The plurality of images can include a plurality of videos. The videos can be obtained from an individual participant in the interactive digital environment, from a plurality of participants in the interactive digital environment, etc.

The flow 100 continues with analyzing emotional content for a first set of participants. In embodiments, the first set of participants are players. In embodiments, the first set of participants are viewers. The flow may include augmenting with audio evaluation 122. Thus, embodiments can include augmenting the analyzing of emotional content, within the plurality of images, with evaluation of audio information. The augmenting with audio evaluation 122 can further refine the analysis of emotional content for the first set of participants 120. In embodiments, the audio evaluation can provide additional context information. For example, detecting shifting in chairs or shuffling of feet can indicate a lack of engagement. Additionally, tones, or voice can indicate a sentiment such as excitement, anger, or surprise. Emotions such as stress can be detected by audio information such as tone and volume. Additionally, the audio evaluation can include language content. For example, a speech-to-text process may be performed to determine if certain keywords are uttered by the participant. The keywords can be used to further analyze the emotional content. For example, if a participant says the word "amazing" then it may be indicative of an emotion of amazement. Thus, in embodiments, the audio information includes voice data.

The flow 100 continues with providing results to a second set of participants 140. In embodiments, the second set of participants are players. In other embodiments, the second set of participants are viewers. The second set of participants thus is provided with an indication of emotional content corresponding to the first set of participants. For example, the first set of participants may be viewers and the second set of participants may be players. In embodiments, the first set of participants substantially matches the second set of participants. For example, the first set and second set may be playing a game together as a team. The players can thus get a sense of the emotional state of the viewers. In particular, the players can get an indication of the level of engagement of the viewers. If the viewers seem engaged, the players may continue with the current level of play. If the viewers seem to be losing interest, the players may try additional tactics, use new weapons/equipment within the game, or other applicable techniques within a game in a shared digital environment to increase engagement of the viewers.

The flow 100 may include analyzing emotional content for the second set of participants 126. Embodiments can include analyzing emotional content within the plurality of images for the second set of participants. The flow 100 may further include providing the results of the analyzing of emotional content for the second set of participants to the first set of participants 142. In such a scenario, each set of participants can receive information regarding an emotional state of the other set of participants. This can make for a more exciting and engaging experience in a shared digital environment, such as with multiplayer gaming, competitive gaming (eSports), or other interactive activity. Thus, embodiments can include providing results of the analyzing of the emotional content within the plurality of images for the second set of participants to the first set of participants.

The flow 100 continues with aggregating results for viewers 160. This can include acquiring a plurality of images for a plurality of viewers, and performing a function to derive a collective emotional state of the plurality of viewers. The function can include identifying a majority emotion. For example, if there are 10,000 viewers, and 7,500 viewers are determined to have an emotion of excitement, then the collective emotional state of the plurality of viewers may be indicated as one of excitement, since more than half of the 10,000 viewers are determined to be exhibiting that state.

The flow 100 may continue with presenting the aggregated results to participants 162, and/or presenting the aggregated results to an individual 164. In some embodiments, the flow 100 may include having a viewer become a player 166. For example, consider a competitive digital game in which participants are competing and viewers are observing. A viewer can become a player in the competitive digital game. The viewer can assume the role of a player within the plurality of participants. Thus, embodiments can include having a viewer, from the plurality of participants become a player within the interactive digital environment. That is, in embodiments, the viewer assumes a role of a player within the plurality of participants. In the case of a competitive digital game, one participant can halt a game, quit a game, leave a game temporarily, etc. One of the viewers of the game can take over play of the game for the previous participant. When a viewer becomes a player, the viewer can receive attributes associated with the player. The attributes that the viewer can receive can include skills, spells, weapons, treasure, hints, keys, and so on. Some viewers can view a live stream while other viewers may participate in an interactive digital environment in a "playback" mode. In embodiments, the viewer can assume the role of the player during a playback of the interactive digital environment. During the playback mode, the viewer can pick up from a previous victory or checkpoint, replay a particularly interesting event in the interactive digital environment, and so on. Thus embodiments can include having a viewer, from the plurality of participants, become a player within the interactive digital environment. In some embodiments, a viewer may be offered an opportunity to become a player based on a detected emotional state of the viewer. For example, if the viewer appears to be engaged or interested based on analysis of images and/or audio of the viewer, then the viewer may be offered an opportunity to become a player so that the individual can try the game that he/she had been viewing. Thus, in embodiments, the viewer assumes a role of a player within the plurality of participants.

Various interactive digital environments can have "free to play" options, "in play" pay options, "pay to play" options, and so on. The digital environments that can have varying free and pay options can include gaming websites, competitive gaming websites, social websites, etc. Participants can pay to join teams, to work cooperatively to solve problems (e.g. join a "guild"), to purchase goods and services, to buy hints for solving problems, and so on.

The flow 100 may include analyzing spending habits 150. In embodiments, when a purchase is made within an interactive activity within a shared digital environment (such as playing an online multiplayer game), a corresponding emotional state is recorded. The corresponding emotional state can be determined from acquired images of the purchaser, and may be further augmented with audio information. In some cases, a participant may be incentivized to enable a user-facing camera and/or microphone to allow capture of image and audio information that is used to determine an emotional state of the participant. In the case where a participant is a player of a game, the purchases may pertain to the game. For example, the purchases can be "in game" purchases that can include purchases of additional weapons for a shooter game, car upgrades for a racing game, healing powers, or virtual currencies (e.g. purchasing gems or gold bars) for purchasing items within the game.

The flow 100 may include associating spending habits with the analysis 152. A sponsor of a site can be interested in analyzing spending habits in order to identify participants in an interactive digital environment who are more likely to spend significant amounts of money while engaged with that digital environment. Such participants, sometimes called "whales" (not always a complimentary term), can be of particular interest to the environment sponsors. The emotional analysis can determine points in a stream, a live stream, a game, a competitive game, and so on, that most correspond to a likelihood that a participant will pay. In embodiments, if it is detected that a user tends to make a purchase when in a particular emotional state, they may be presented with an advertisement for a purchase upon detecting that emotional state. For example, if a participant has previously purchased virtual "weapons" for a game when in an angry emotional state, then the participant may be prompted to purchase some virtual weapons for the game at a future time when an emotional state of anger is detected on the participant. Embodiments can include analyzing spending habits of a third set of participants within the plurality of participants. Embodiments can include associating the spending habits of the third set of participants with results of emotional analysis for the third set of participants. In embodiments, the plurality of participants is involved in live streaming of the interactive digital environment. In some embodiments, viewers can buy items for players. A fan could purchase a tool or capability for a favorite or preferred player. Analysis of viewers' emotional perspective can be used to evaluate suggesting such a purchase. In some cases, a slightly distressed viewer could be asked, "Would you like to pay $1 to give your favorite player a chaingun?" but for a very distressed viewer it could say, "Would you like to pay $20 to give your favorite player a chaingun?" Other incentives and capabilities or tools could be utilized by viewers and players of a digital game.

The flow 100 may continue with modifying the environment 170. Embodiments can include modifying the interactive digital environment based on results of the analyzing of the emotional content. Embodiments can include modifying the shared digital environment based on the spending habits of the third set of participants and the results of emotional analysis for the third set of participants. This can include adding or deleting of players and/or viewers, as well as adding additional game content such as weapons, vehicle upgrade, additional lives, additional virtual currency, or other suitable add-ons, all for the augmentation of the game. In embodiments, a competitive digital game could be modified dynamically to feature more events that were pleasing to most users, and to remove or make less frequent events that resulted in boredom, anger, etc. Similarly, emotional data can simplify discovering what current users already like and can focus marketing on the content that provides the biggest emotional impact, thus increasing the chance of adoption. The modifying the interactive digital environment can be used for viewing experiences including virtual reality and augmented reality. Such modification could include providing events and scenarios that emotional data indicate are the most pleasant, pleasing, relevant, interesting, etc. to the viewers. The modifying can include changing video to a head mounted virtual reality (VR) display, audio to headphones, steps in the games, plays in the game, and so on. The modifying the interactive digital environment could extend to sharing of a viewer's experience to the viewer's social network. Such sharing could include, with the user's permission, pre-populating a social media post. One such post could include saying "I loved this 'Defense of the Ancients™' (DoTA) game. Relive my highlights by clicking here." The user could share the pre-populated post as-is or could personalize it. Other options could include links to the stream or links to other popular streams for the same game. In another example, emotional data could influence organic growth by making recommendations to viewers. Recommendations could include telling viewers, "According to our records, you enjoyed this session more than any other. Would you like to share this session with your friends on your favorite social networking site?"

The providing of the results of the analyzing of the emotional content within the plurality of images can be used to edit a live stream. Editing a live stream can be performed to create a "highlights reel" of key events in a video live stream, to customize a live stream's contents, and so on. For example, an editor can use the results of the analyzing emotional content to pick the points in a live stream where a viewer was happiest. Similarly, the editor could choose to include bloopers corresponding to smirks for comedic effect, could omit events in the live stream that caused frowns or boredom, and so on. Broadcasters could use the results of analyzing of the emotional content to expand services to viewers of and subscribers to a given interactive digital environment.

Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors. Various embodiments of the flow, or portions thereof, 100 can be included on a semiconductor chip and implemented in special purpose logic, programmable logic, and so on.

Figure 2:
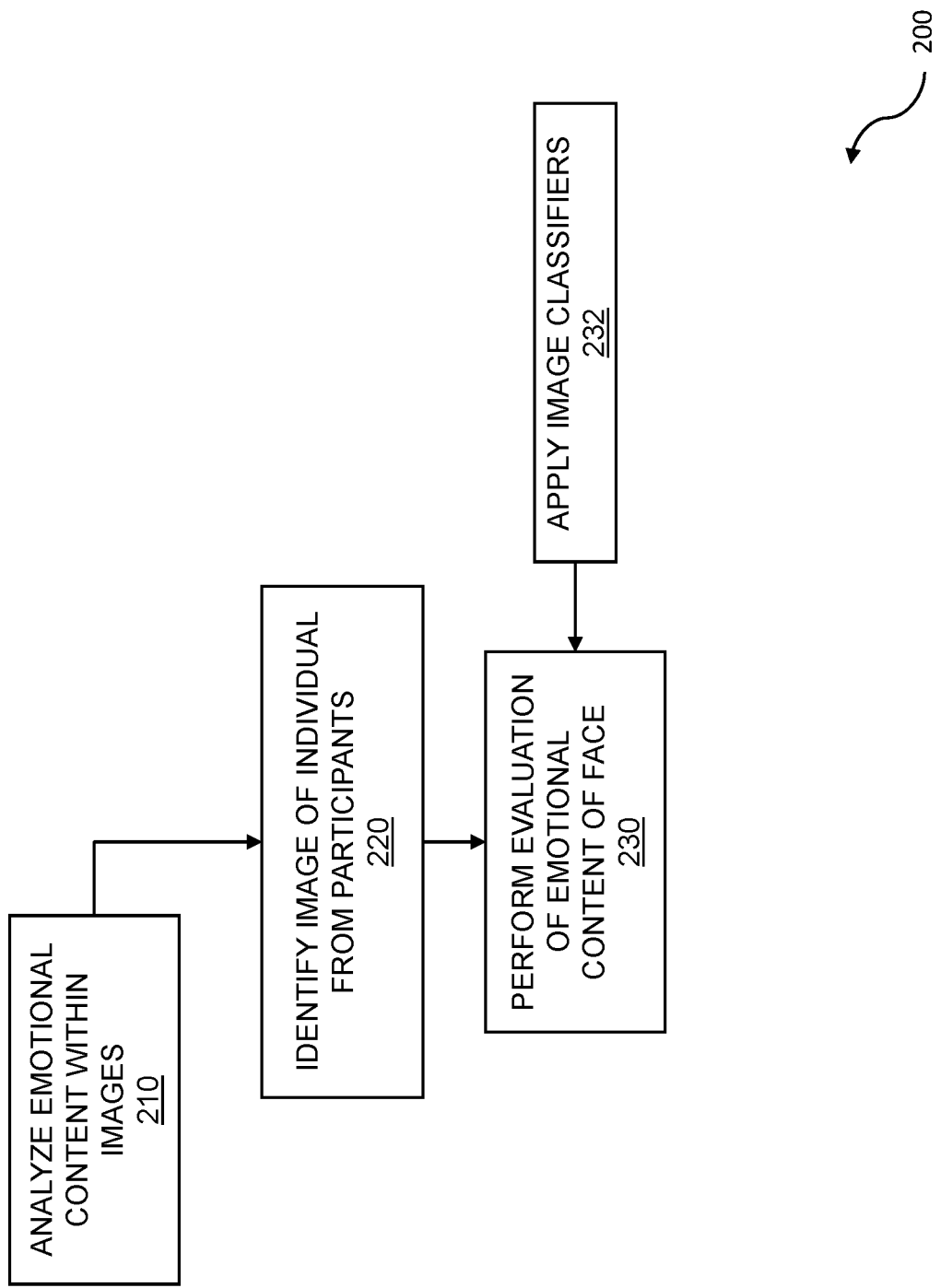
FIG. 2 is a flow diagram for analyzing emotional content.

FIG. 2 is a flow diagram for analyzing emotional content. The flow 200 includes analyzing emotional content within images 210. In embodiments, the analyzing emotional content within the plurality of images comprises identifying an image of an individual within the plurality of participants 220; and performing an evaluation of emotional content of a face for the individual based on applying image classifiers to the image. The flow 200 includes identifying an image of an individual from the plurality of participants 220. A given image that is obtained can include one or more objects, animals, people, etc. When a person is found in the image, the face of the individual is identified within the image. The face can be identified in the image using a variety of image processing and analysis techniques including edge detection, gradient calculation, and so on. A bounding box can be placed around the face to indicate the location of the face. The flow 200 continues with performing an evaluation of emotional content of a face 230 within an image. In embodiments, there is an evaluation of facial content based on applying image classifiers 232 to regions within the face of the individual. The classifiers can be used to detect moods, emotional states, mental states, and so on. The evaluation of content of the face can include detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, poignancy, drowsiness, or mirth. Thus, in embodiments, analyzing of the emotional content includes detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, poignancy, drowsiness, or mirth.

Figure 3:
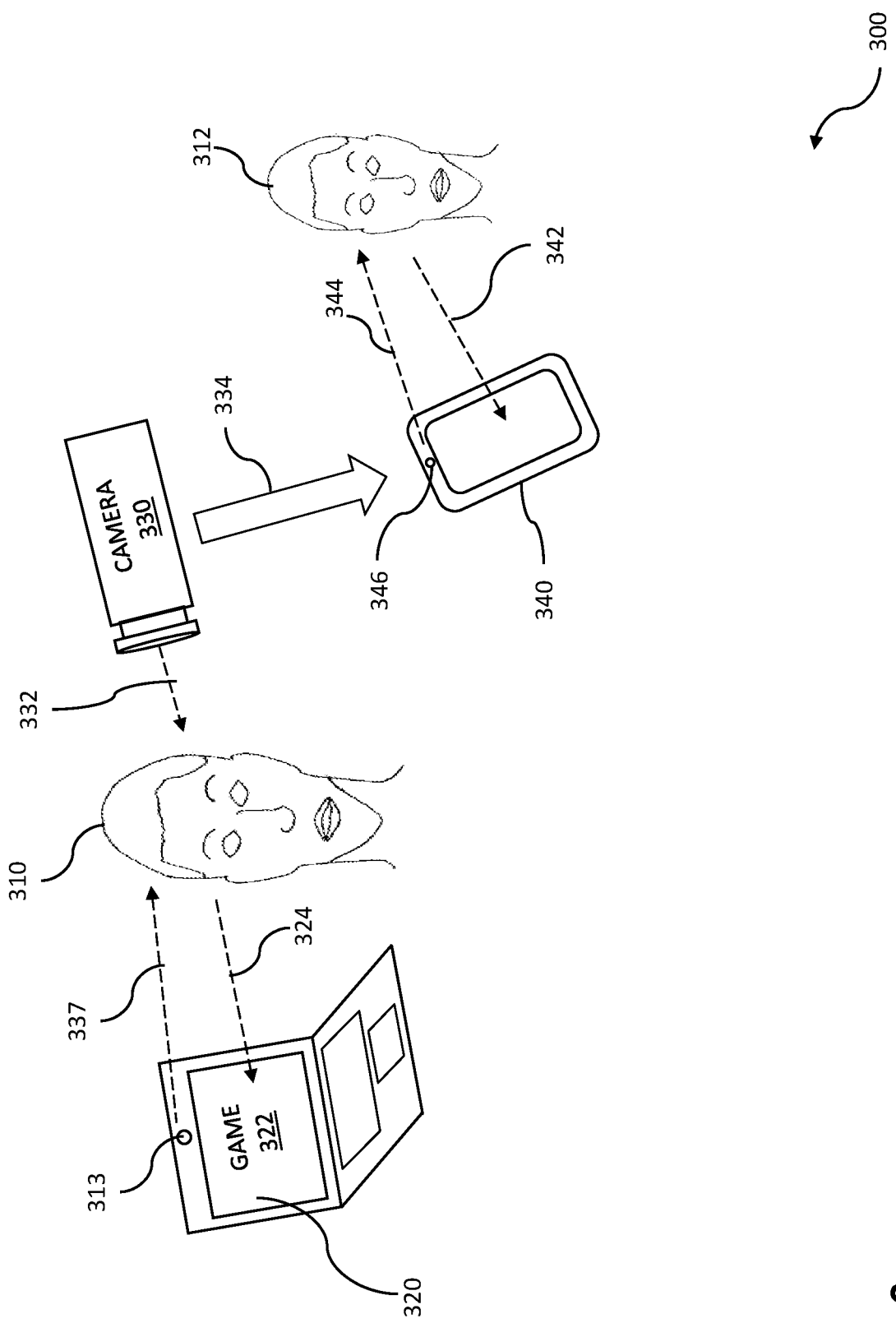
FIG. 3 is a diagram showing player and viewer interaction.

FIG. 3 is an example 300 showing a player and a viewer. Video of a participant 310 involved in an interactive digital environment including a digital game can be live streamed to a viewer 312. The participant 310 has a line of sight 324 to a game 322 rendered on a display 320. In this example, the participant 310 is a player. The game can be a video game, a competitive video game, and so on. A plurality of images can be obtained from the participant involved in an interactive digital environment using an integrated user-facing camera 313 or a standalone user-facing camera 330. The camera 330 has a line of sight 332 to the participant 310. The camera 313 has line of sight 337 to the participant 310.

The cameras 313 and/or 330 can be any of a variety of cameras. A camera can include a webcam, a video camera, a still camera, a thermal imager, a CCD device, a phone camera, a three-dimensional camera, a depth camera, a light field camera, multiple webcams used to show different views of a person from different angles, or any other type of image capture apparatus that can allow captured data to be used in an electronic system. The image can be a still image, a frame from a video, a video, and so on. The image can be one image from a series of images of the individual. The series of images can include a video of the individual. Emotional content can be analyzed within the plurality of images for the participant 310. The results of the analyzing of the emotional content within the plurality of images can be provided 334 (e.g. via a network communication protocol) to a set of participants within the larger group of participants. The results of the analyzing of the emotional content can be provided to viewers of the interactive digital environment. A viewer 312 has a line of sight 342 to a screen on a device 340. The device can be a handheld device, a portable device, a laptop computer, a television screen, etc. A camera 346 coupled to the device 340 can have a line of sight 344 to the viewer 312, and can be used for obtaining a plurality of images from the viewer 312. The emotional content of the images of the viewer 312 can be shared with participants, viewers, and so on.

Figure 4:
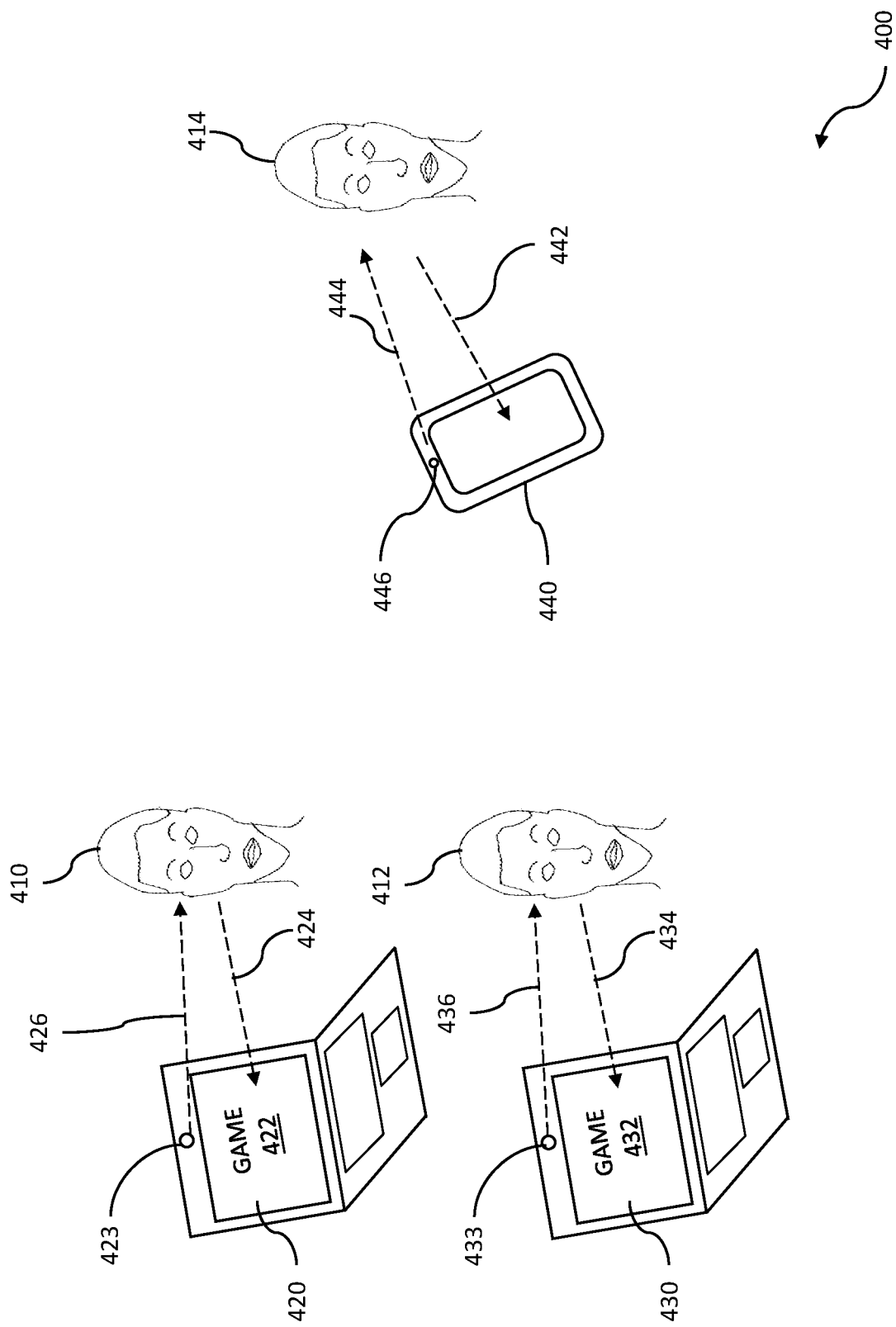
FIG. 4 illustrates two players as well as a viewer among participants.

FIG. 4 shows an example 400 with two players as well as a viewer among participants. In the example 400, a first participant 410 and a second participant 412 are players. The participant 410 has a line of sight 424 to a game 422 rendered on a display 420. In this example, the participant 410 is a player. The game can be a video game, a competitive video game, and so on. A plurality of images can be obtained from the participant involved in an interactive digital environment using an integrated user-facing camera 423. The camera 423 has a line of sight 426 to the participant 410. Similarly, participant 412 has a line of sight 434 to a game 432 rendered on a display 430. In this example, the participant 412 is a player. A plurality of images can be obtained from the participant involved in an interactive digital environment using an integrated user-facing camera 433. The camera 433 has a line of sight 436 to the participant 412. In embodiments, the participants 410 and 412 are both players that are playing a game together. Hence, in embodiments, game 422 and game 432 may be the same game. In some embodiments, the rendering on display 420 and display 430 may be identical. In other embodiments, the rendering on display 420 and 430 may be different. For example, in a first-person shooter game, each display may render a point-of-view corresponding to that player. Thus, display 420 may render a point-of-view corresponding to participant 410, and display 430 may render a point-of-view corresponding to participant 412. In some embodiments, participant 410 and participant 412 may be playing against each other, such as playing or coaching soccer or football against each other, racing against each other, or other head-to-head gaming activity. In other embodiments, participant 410 and participant 412 may be playing with each other, as part of the same team in a game taking place in an interactive digital environment.

A third participant 414 can be a viewer, watching the game play between participant 410 and participant 412 on an electronic device 440. The viewer has a line of sight 442 to the electronic device 440. The electronic device 440 may have a user-facing camera 446. The camera 446 has a line of sight 444 to the participant 414.

In embodiments, the emotional state of each participant may be computed by analyzing one or more images from the corresponding user-facing camera of each viewer. Additionally, audio information may be used to augment the emotional state analysis. In some embodiments, when two players are competing against each other, each player may be presented with an emotional state indication of the other player. In embodiments, the emotional state indication may be a graphical element, such as an emotion meter. Thus, each player can get an indication of how the other player is feeling during the game play. In some embodiments, the viewer (participant 414) can receive an indication of how each of the players are feeling. In embodiments, there may be an emotion meter rendered for each player of the game that the viewer is watching. In embodiments, the emotional state of the viewer may be presented to players such as participant 410 and/or participant 412. In this way, the players can receive information about the mood and/or engagement of the viewer.

Figure 5:
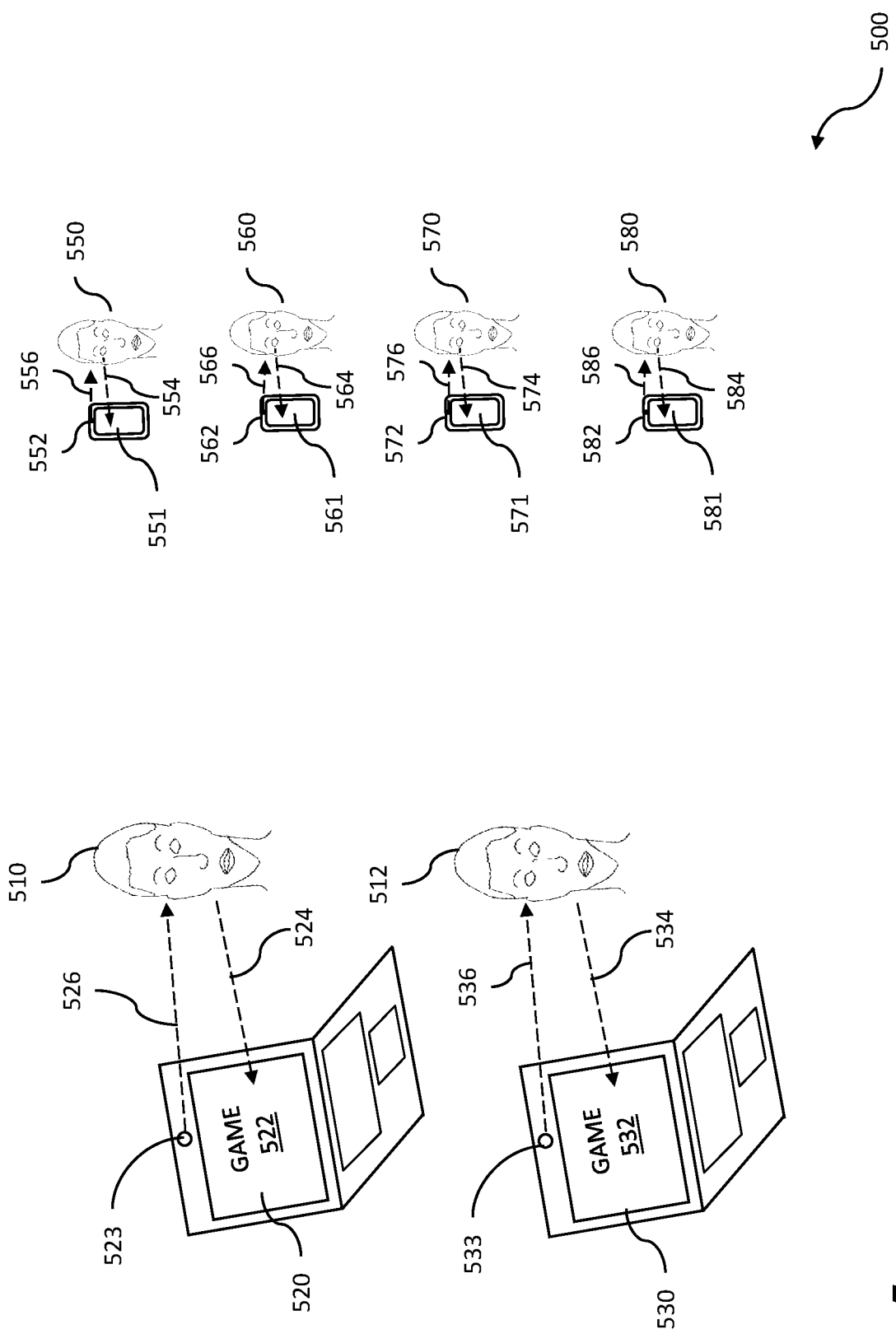
FIG. 5 shows two players and multiple viewers.

FIG. 5 shows an example 500 with two players and multiple viewers. In the example 500, a first participant 510 and a second participant 512 are players. Participants 550, 560, 570, and 580 are viewers. The participant 510 has a line of sight 524 to a game 522 rendered on a display 520. In this example, the participant 510 is a player. The game can be a video game, a competitive video game, and so on. A plurality of images can be obtained from the participant involved in an interactive digital environment using an integrated user-facing camera 523. The camera 523 has a line of sight 526 to the participant 510. Similarly, participant 512 has a line of sight 534 to a game 532 rendered on a display 530. In this example, the participant 512 is a player. A plurality of images can be obtained from the participant involved in an interactive digital environment using an integrated user-facing camera 533. The camera 533 has a line of sight 536 to the participant 512. In embodiments, the participants 510 and 512 are both players that are playing a game together. Hence, in embodiments, game 522 and game 532 may be the same game. In some embodiments, the rendering on display 520 and display 530 may be identical. In other embodiments, the rendering on display 520 and 530 may be different. For example, in a first-person shooter game, each display may render a point-of-view corresponding to that player. Thus, display 520 may render a point-of-view corresponding to participant 510, and display 530 may render a point-of-view corresponding to participant 512. In some embodiments, participant 510 and participant 512 may be playing against each other, such as playing or coaching soccer or football against each other, racing against each other, or other head-to-head gaming activity. In other embodiments, participant 510 and participant 512 may be playing with each other as part of the same team in a game taking places in an interactive digital environment.

Participant 550 is a spectator that is viewing the game between participant 510 and participant 512. Participant 550 has a line of sight 554 to electronic device 551. Electronic device 551 includes camera 552, which has line of sight 556 to the participant 550. Similarly, participant 560 has a line of sight 564 to electronic device 561. Electronic device 561 includes camera 562, which has line of sight 566 to the participant 560, participant 570 has a line of sight 574 to electronic device 571. Electronic device 571 includes camera 572, which has line of sight 576 to the participant 570. Participant 580 has a line of sight 584 to electronic device 581. Electronic device 581 includes camera 582, which has line of sight 586 to the participant 580.

In embodiments, each spectator (550, 560, 570, and 580) may have their emotional state determined by images acquired by their respective user-facing cameras. Additionally, audio information from a microphone (not shown) may be used to further enhance and refine the emotional state analysis. In embodiments, the emotional state of each viewer may be averaged or otherwise combined to form an aggregate emotional state, representative of a collective emotional state of the viewers. The aggregate emotional state may be presented to participant 510 and participant 512 as players, so that the players can receive an indication of the overall emotional state of the "crowd" that includes the plurality of viewers (550, 560, 570, and 580). In this way, the players (510, 512) can make modifications to the game in response to the determined emotional state of the crowd. For example, if the crowd seems disengaged, the players (510, and 512) can make changes to the game to make it more interesting (e.g. add new weapons in the game). Similarly, each viewer in the crowd may receive an indication of the emotional state of the players to get a sense of what each player is currently feeling, which can add a level of excitement/interest to watching the gameplay.

Figure 6:
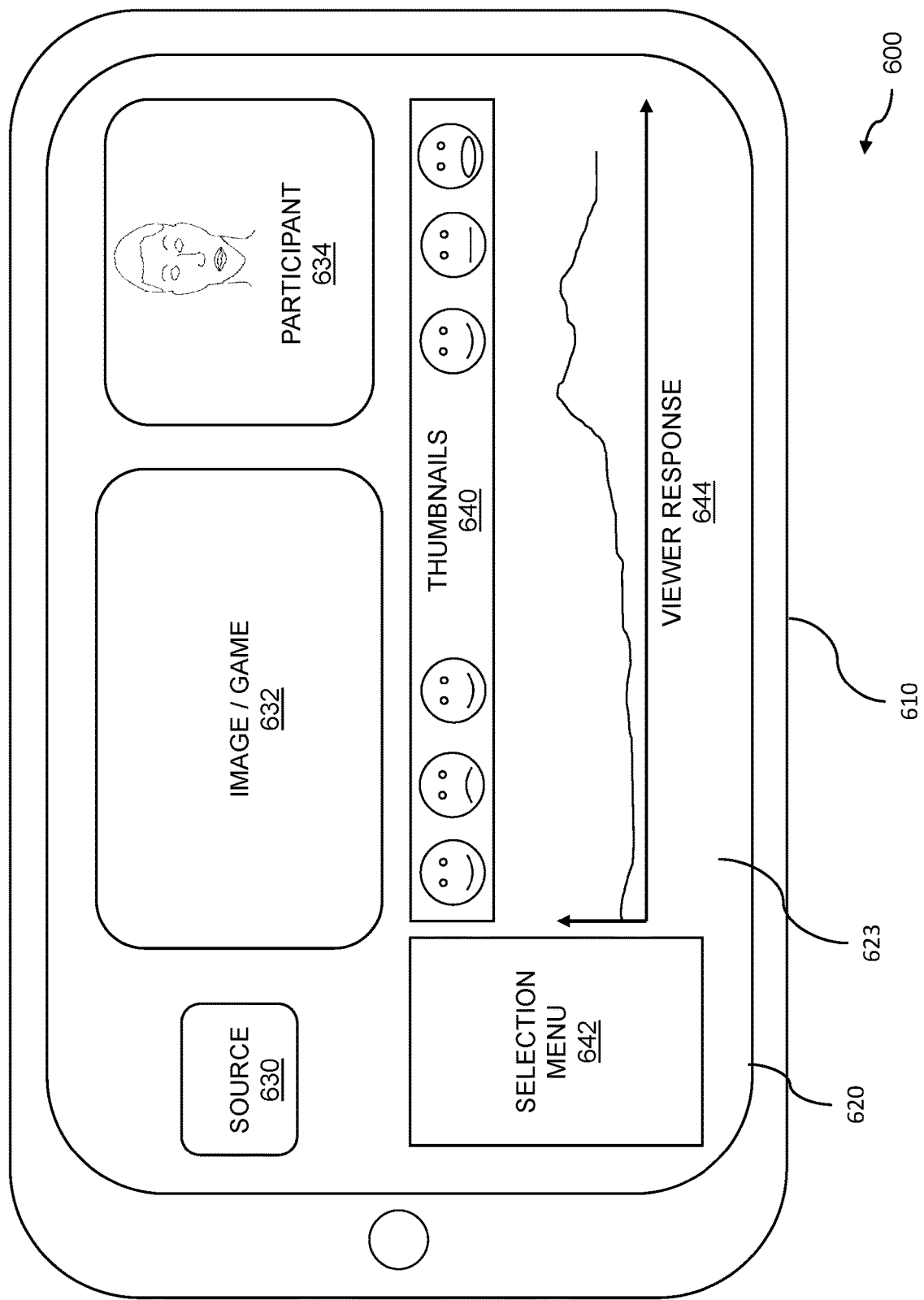
FIG. 6 illustrates viewer responses to games.

FIG. 6 shows an example 600 showing viewer responses to a game. An electronic device 610 includes a display 620, which includes a user interface 623. The user interface may be part of a games research tool. The user interface may include a rendering of a game 632 and/or images pertaining to the game. The user interface may include a source 630. A source can be a live stream of a video game, a video game competition, a "highlights reel" of a competition, a suggested video presented to the viewer, based on a viewer's past viewing preferences or their emotional responses to similar video content, and so on. The video, image, game, competition, etc. can be displayed in a dashboard or other rendering technique, along with images of viewers, statistics for an individual viewer, aggregated viewer responses, and so on. In embodiments, the user may be able to select a source from amongst a plurality of different sources. In embodiments, the different sources represent different games.

The user interface 623 may include a selection menu 642. The selection menu 642 can enable filtering of the source information. In embodiments, the selection menu 642 can include demographics information. Selection options from selection menu 642 may include, but are not limited to, participant type (viewer or player), age group (e.g. less than 18 years old, 18 to 34 years old, 35 to 49 years old, and 50 years or older), skill level (e.g. novice, intermediate, master), and/or geographic location (e.g. North America, Asia, Europe, etc.).

An image of a person can be shown, where the person can be a participant 634 in a game, competition, etc.; the person is a viewer or player of the game, competition, etc.; and so on. The image of the person can be a still image, a video, a video clip, a highlights reel, etc. The image of the person can be an avatar controlled by a game player, a participant, a viewer, etc. The image of the person or avatar can change when a viewer assumes the role of the player during a playback of an interactive digital environment. For example, a novice player of a game may wish to try an advanced level of a game, but he/she may not have the skill to reach an advanced level. In embodiments, the novice player may participate as a player in an advanced level by entering a previously played game as a player by entering the game at a certain point during the playback of the previously played game. The digital environment can be part of a virtual reality environment. The digital environment can be part of an augmented reality environment. In embodiments, the digital environment can be modified based on the detected emotional state of a player. For example, if a player seems bored while playing a game, the digital environment in which the game is played can be modified to make the game harder, creating a greater challenge for the player.

The user interface may include a plurality of thumbnails 640. The thumbnails can include images of participants in a game. The participants can be viewers and/or players. In some embodiments, a user of the electronic device 610 can select a thumbnail to display in the window allocated for participant 634, which enables getting a closer look at a participant.

The user interface 623 may include a viewer response graph 644. The viewer response graph 644 may show an emotional response as a function of time. The emotional response can be for an individual, or a collective emotional response of a group of people. In embodiments, the emotional response can be for one or more players, one or more viewers, or a collective emotional response of a group that includes both players and users. The user interface 623 provides useful analytical information about the engagement level of a game within a shared digital environment. The engagement level can be a useful tool in determining appropriate advertising rates, gaming fees, and/or content licensing fees.

Figure 7A:
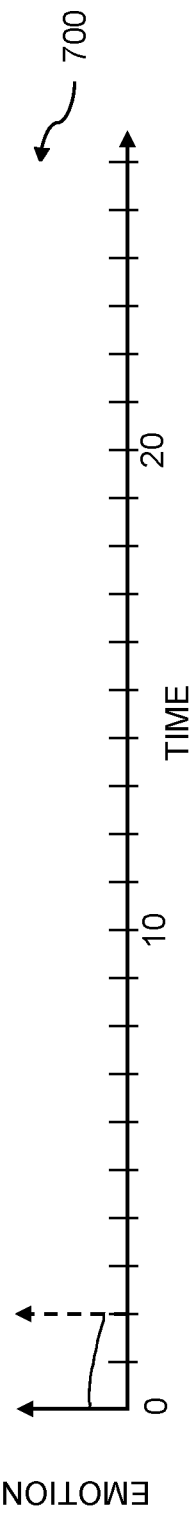
FIGS. 7A-7C show examples of emotional states as a function of time.
Figure 7B:
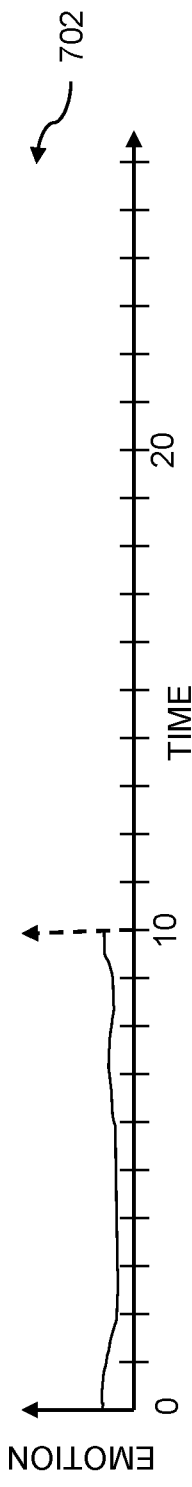
Figure 7C:
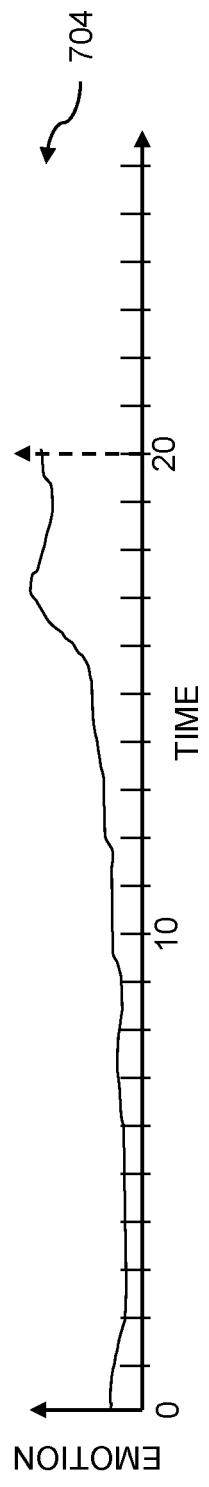

FIGS. 7A-7C show an emotional state graph at various times. FIG. 7A shows an emotional state graph 700 until a time of two seconds (t=2). FIG. 7B shows an emotional state graph 702 until a time of ten seconds (t=10). FIG. 7C shows an emotional state graph 704 until a time of 20 seconds (t=20). Thus, the horizontal axis of each emotional state graph represents time (e.g. in seconds, minutes, or other appropriate time unit). The vertical axis of each emotional state graph represents an emotion intensity. The emotion intensity can be based on action units, image classifiers, shape analysis, audio information, and/or other suitable sources. The emotional state graphs can be used to correlate with particular periods of game play to determine game scenarios that are associated with a particular emotional state (e.g. surprise, anguish, drowsiness, etc.). In this way, information can be gathered about what parts of a game are effective in engagement with viewers, and/or which player participants successfully engage viewers, and other valuable metrics and analytics for identifying valuable gaming content.

Figure 8:
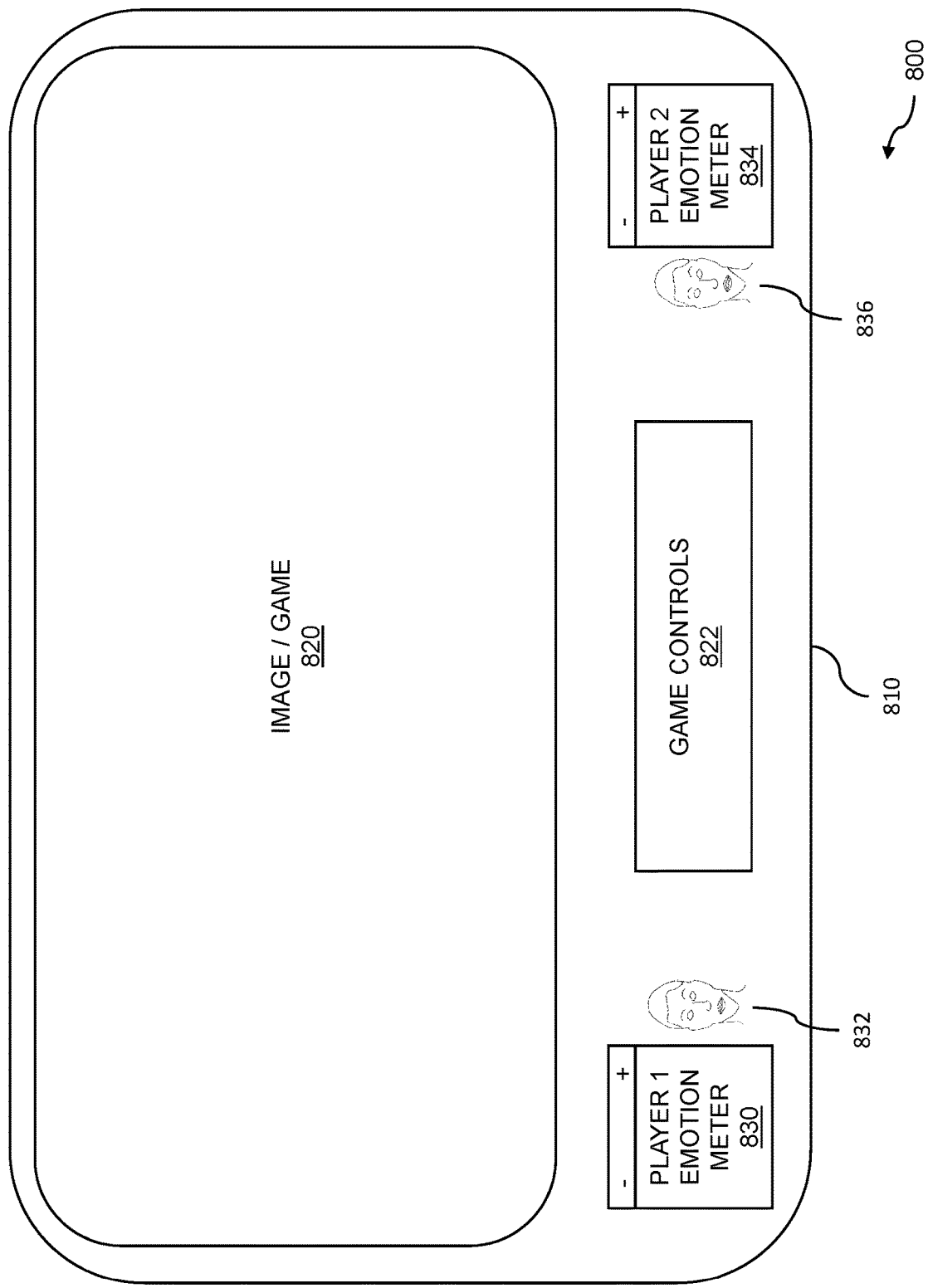
FIG. 8 shows an interactive digital environment with player emotion meters.

FIG. 8 shows an example 800 of an interactive digital environment with player emotion meters. The example 800 may be rendered on a screen 810 such as a tablet computer screen, laptop screen, mobile phone screen, desktop screen, television screen, or other suitable display monitor. The example 800 includes an image/game area 820 showing game play and/or images associated with game play in an interactive digital environment. One or more game controls 822 may be provided for playing of the game. A first player 832 has a corresponding emotion meter 830, and a second player 836 has a corresponding emotion meter 834. In embodiments, the emotion meters 830 and 834 operate simultaneously to render an emotional state of each player based on the analysis of acquired images and/or associated audio of the players. In embodiments, the first player 832 and the second player 836 each view a similar example 800, and as they play the game, each player can get an indication of the emotional state of the other player. For example, if the first player 832 is on the verge of defeating the second player 834, then the emotion meter of the second player may indicate an emotion of anger or frustration, and a corresponding level, and the emotion meter of the first player 832 may indicate an emotion of happiness, and a corresponding level.

Figure 9:
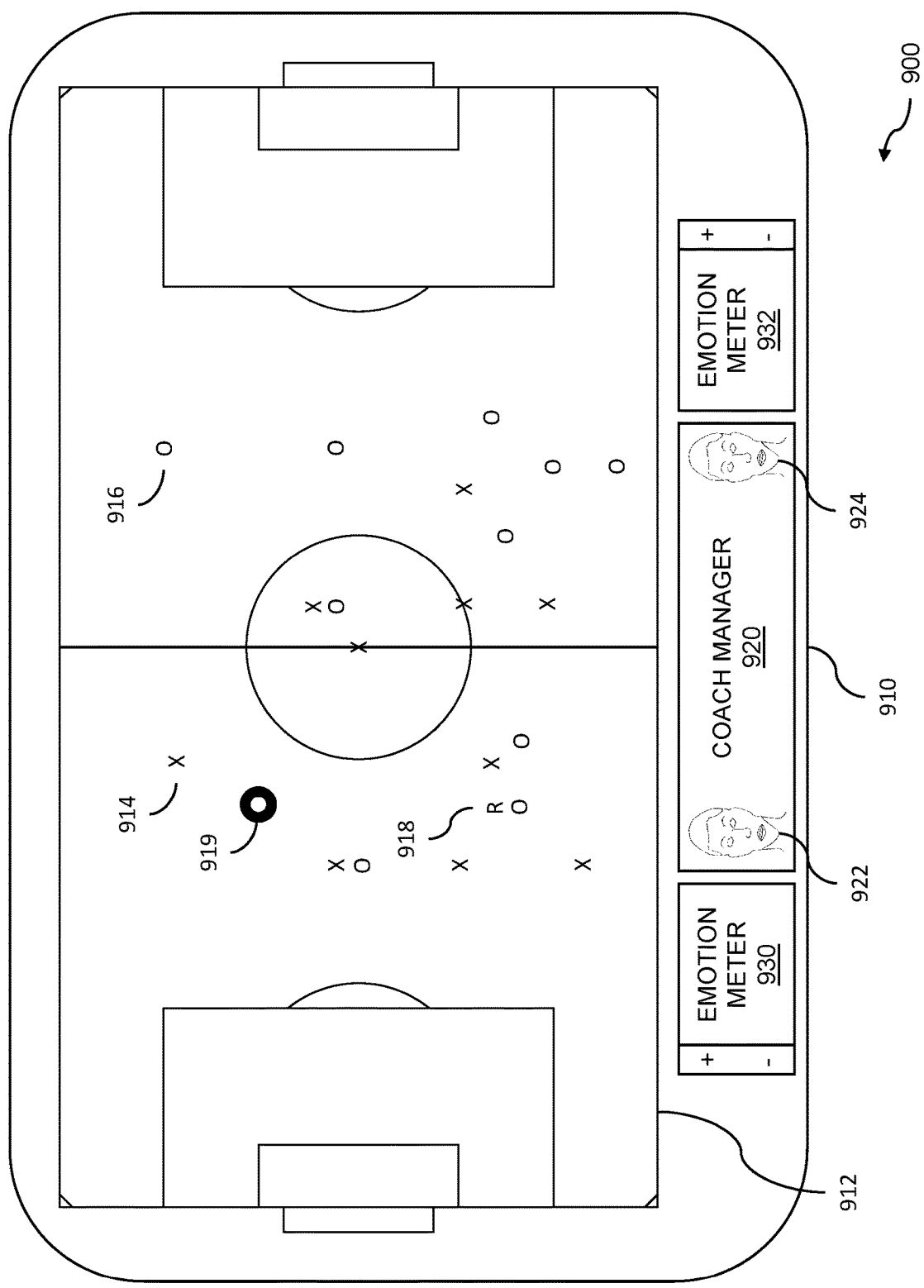
FIG. 9 illustrates an interactive digital environment with coach emotion meters.

FIG. 9 shows an example 900 of an interactive digital environment with coach emotion meters. The example 900 may be rendered on a display 910 such as a tablet computer screen, laptop screen, mobile phone screen, desktop screen, television screen, or other suitable display monitor. The example 900 includes an image/game area 912 showing a digital soccer game in an interactive digital environment. A coach (manager) field 920 shows a first coach 922 and a second coach 924. A first emotion meter 930 corresponds to the emotions of first coach 922. A second emotion meter 932 corresponds to second coach 924. The coaches may be in control of a team of virtual players. The first team players are indicated generally at 914 by the "X" symbol. The second team players are indicated generally at 916 by the "O" symbol. A referee may be indicated at 918 by the "R" symbol. A soccer ball is indicated at 919. As the coaches control their respective teams, a user-facing camera can capture images of each coach and render an indication on the corresponding emotion meter. In this way, each coach can receive an indication of the emotional state of the other coach, further enhancing the gaming experience.

Figure 10:
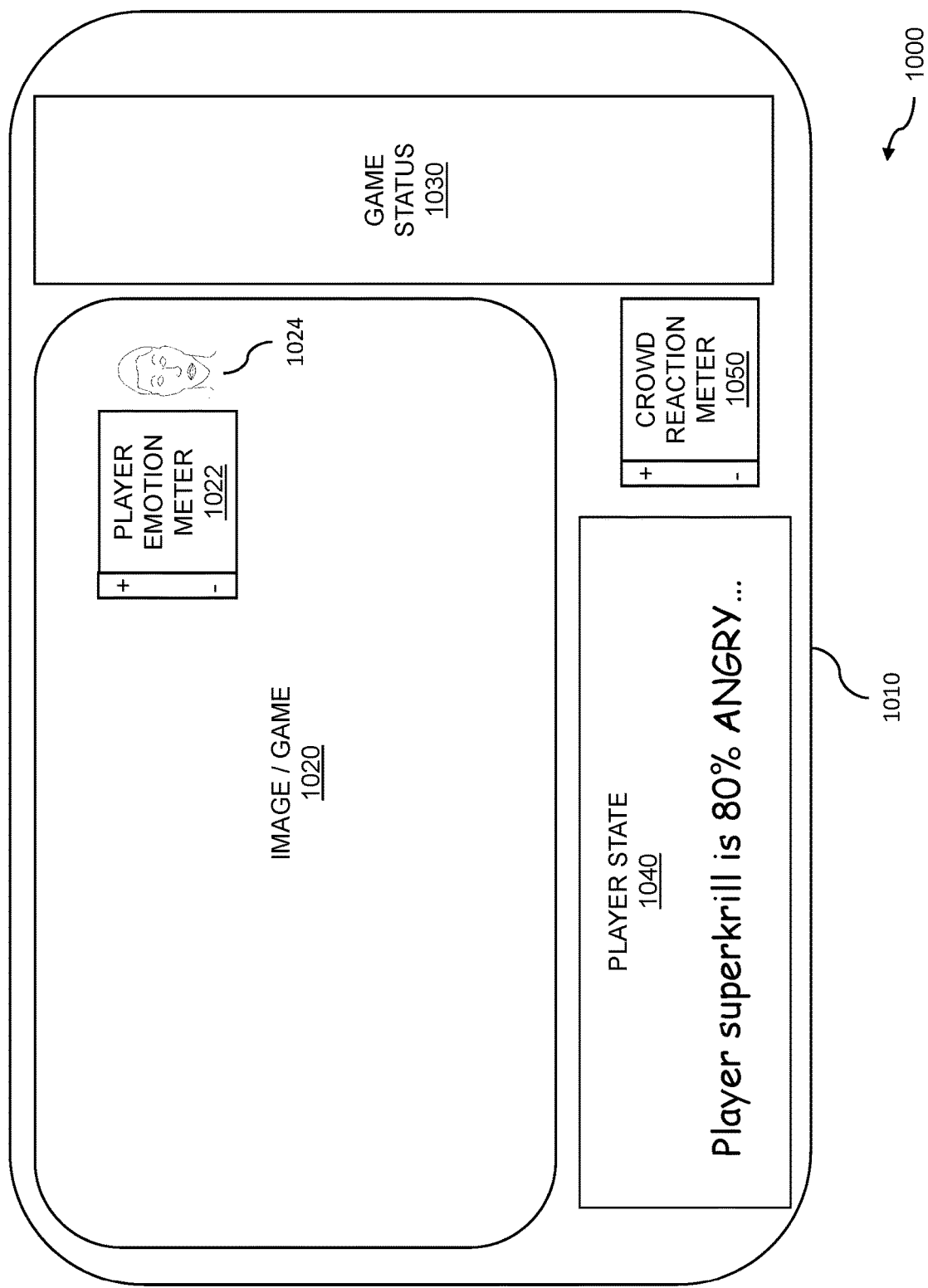
FIG. 10 illustrates spectator and player emotion meters.

FIG. 10 illustrates an example 1000 with spectator and player emotion meters. This example is particularly well suited for competitive sports (eSports). In embodiments, the interactive digital environment includes a competitive digital game. Example 1000 includes a display 1010 with multiple fields. Field 1020 shows game play and/or images associated with game play. The game can be an interactive multiplayer game, such as a shooter game, racing game, fantasy game, combat game, strategy game, sports game, card game, word puzzle game, digital board game, or other suitable game. The display 1010 includes a player emotion meter 1022 and a video rendering 1024 showing the player. The player emotion meter 1022 can indicate a level of intensity of a particular emotion. Field 1030 shows a game status. The game status can include comments on the game from viewers, current scores of the game, and/or other game statistics. Field 1040 shows a player state. The player state may indicate an emotion of a player and the corresponding level of that emotion.

The display 1010 includes a crowd reaction meter 1050. The crowd can include a plurality of participants in the same room. Alternatively, the crowd can include a plurality of participants in different locations observing the display 1010 on their own electronic devices via a computer network. Each member of the crowd can have a corresponding electronic device with a user-facing camera that can collect a video of the member (participant). Thus, embodiments can include multiple cameras covering multiple people to create a plurality of videos. The crowd reaction meter 1050 can indicate a level of positive or negative sentiment of a plurality of viewers. This can be derived by collecting images of multiple viewers, and determining an overall positive or negative sentiment based on facial analysis and/or audio analysis. As an example, smiles may indicate a positive sentiment while frowns may indicate a negative sentiment. The level or intensity of the emotion can contribute to the scoring that is rendered in the crowd reaction meter 1050. For example, a mild smile can be worth +1 points, a moderate smile can be worth +2 points, and a wide smile can be worth +3 points. Similarly, a mild frown can be worth −1 points, a moderate frown can be worth −2 points, and an intense frown can be worth −3 points. The points from each analyzed participant in the crowd can be totaled on a periodic basis (e.g. every 5 seconds) and the crowd reaction meter can be periodically updated with a new score based on the new total. In this way, the player may receive an indication of a crowd reaction via the crowd reaction meter 1050. Similarly, the crowd may receive an indication of the player emotional state via information displayed in the player state field 1040 along with the player emotion meter 1022 and player video rendering 1024. Being able to observe the emotional state of various participants can enhance the overall gaming/entertainment experience for the participants. Thus, embodiments include aggregating results of the analyzing the emotional content within the plurality of images for a set of viewers within the plurality of participants. Embodiments can include presenting results of the aggregating to an individual within the plurality of participants. Embodiments can include presenting results of analyzing emotional reaction, to the interactive digital environment, for the individual to the individual.

Figure 11:
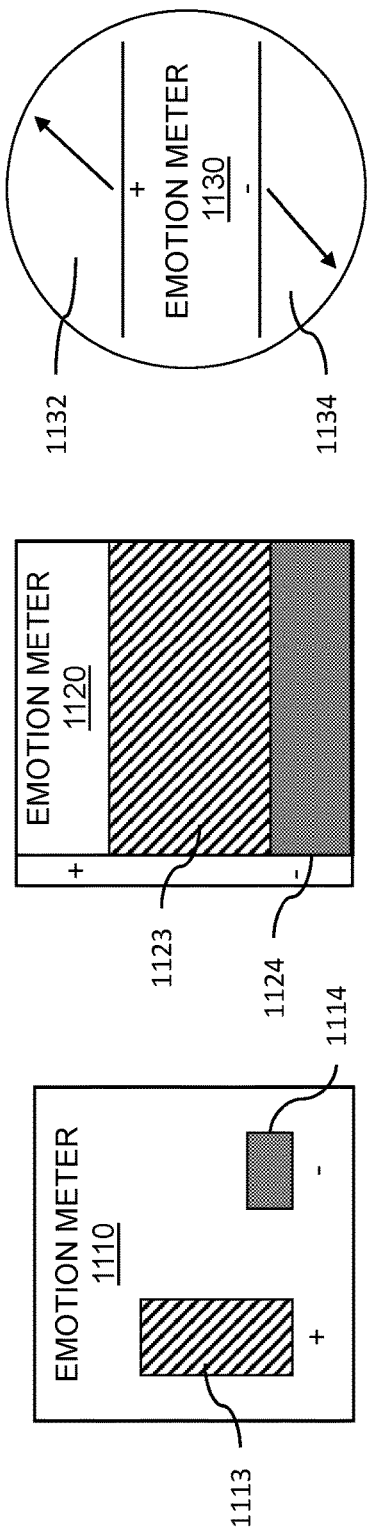
FIG. 11 shows various emotion meters.
Figure 11:
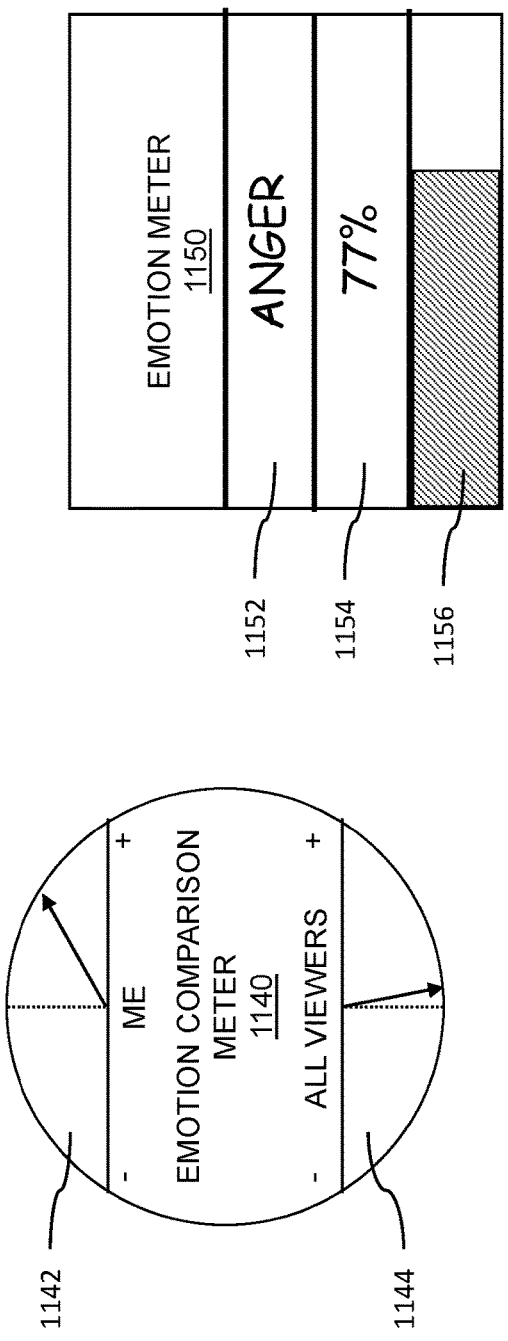

FIG. 11 shows various emotion meters that can be used in disclosed embodiments. Emotion meter 1110 is a bar graph style emotion meter with a bar 1113 for positive sentiment (emotion) and a bar 1114 for negative sentiment. Emotion meter 1120 is a stacked bar graph style emotion meter with a bar 1123 for positive sentiment and a bar 1124 for negative sentiment. Emotion meter 1130 is a gauge style emotion meter with a gauge 1132 for positive sentiment and a gauge 1134 for negative sentiment. Emotion comparison meter 1140 indicates sentiment for both an individual and a crowd. The gauge 1142 indicates sentiment for an individual and the gauge 1144 indicates sentiment for the crowd. Emotion meter 1150 comprises an emotion identification field 1152 that displays a detected emotion, a numerical emotion intensity field 1154 that displays a numerical intensity of the emotion shown in field 1152, and a graphical representation of the emotion intensity 1156. These emotion meters are merely exemplary, and other emotion meters are possible for use in disclosed embodiments.

Figure 12:
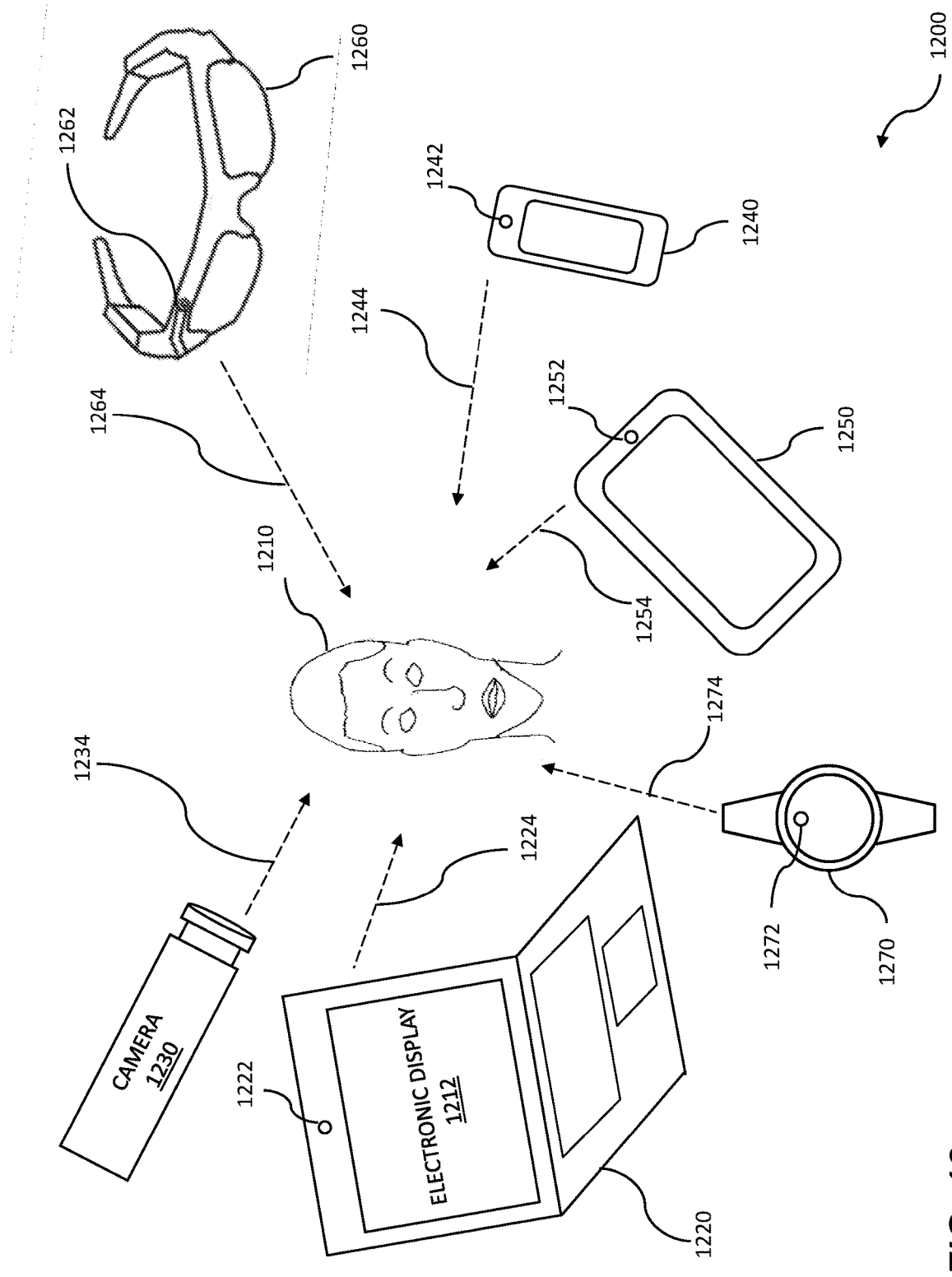
FIG. 12 is a diagram showing image collection including multiple mobile devices.

FIG. 12 is a diagram showing image collection using multiple mobile devices. The collected images can be evaluated for an individual to be within a sub-sectional component of a population. The sub-sectional components can be used with performing the evaluation of content of the face. The sub-sectional components can be used to provide a context. In the diagram 1200, the multiple mobile devices can be used singly or together to collect video data on a user 1210. While one person is shown, the video data can be collected on any number of people. A user 1210 can be observed as she or he is performing a task, experiencing an event, viewing a media presentation, and so on. The user 1210 can be shown one or more media presentations, political presentations, or social media, or another form of displayed media. The one or more media presentations can be shown to a plurality of people. The media presentations can be displayed on an electronic display 1212 or another display. The data collected on the user 1210 or on a plurality of users can be in the form of one or more videos, video frames, still images, etc. The plurality of videos can be of people who are experiencing different situations. Some example situations can include the user or plurality of users being exposed to TV programs, movies, video clips, social media, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1210 can be analyzed and viewed for a variety of purposes including expression analysis, mental state analysis, and so on. The electronic display 1212 can be on a laptop computer 1220 as shown, a tablet computer 1250, a cell phone 1240, a television, a mobile monitor, or any other type of electronic device. In one embodiment, expression data is collected on a mobile device such as a cell phone 1240, a tablet computer 1250, a laptop computer 1220, or a watch 1270. Thus, the multiple sources can include at least one mobile device, such as a phone 1240 or a tablet 1250, or a wearable device such as a watch 1270 or glasses 1260. A mobile device can include a forward-facing camera and/or a rear-facing camera that can be used to collect expression data. Sources of expression data can include a webcam 1222, a phone camera 1242, a tablet camera 1252, a wearable camera 1262, and a mobile camera 1230. A wearable camera can comprise various camera devices such as the watch camera 1272.

As the user 1210 is monitored, the user 1210 might move due to the nature of the task, boredom, discomfort, distractions, or for another reason. As the user moves, the camera with a view of the user's face can be changed. Thus, as an example, if the user 1210 is looking in a first direction, the line of sight 1224 from the webcam 1222 is able to observe the user's face, but if the user is looking in a second direction, the line of sight 1234 from the mobile camera 1230 is able to observe the user's face. Furthermore, in other embodiments, if the user is looking in a third direction, the line of sight 1244 from the phone camera 1242 is able to observe the user's face, and if the user is looking in a fourth direction, the line of sight 1254 from the tablet camera 1252 is able to observe the user's face. If the user is looking in a fifth direction, the line of sight 1264 from the wearable camera 1262, which can be a device such as the glasses 1260 shown and can be worn by another user or an observer, is able to observe the user's face. If the user is looking in a sixth direction, the line of sight 1274 from the wearable watch-type device 1270, with a camera 1272 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1210 can also use a wearable device, including a camera, for gathering contextual information and/or collecting expression data on other users. Because the user 1210 can move her or his head, the facial data can be collected intermittently when she or he is looking in a direction of a camera. In some cases, multiple people can be included in the view from one or more cameras, and some embodiments include filtering out faces of one or more other people to determine whether the user 1210 is looking toward a camera. All or some of the expression data can be continuously or sporadically made available from the various devices and other devices.

The captured video data can include facial expressions and can be analyzed on a computing device such as the video capture device or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 13:
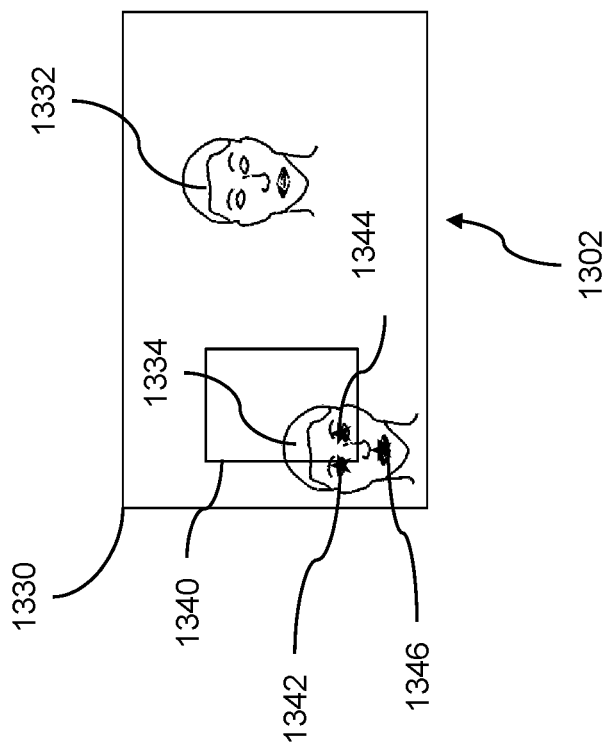
FIG. 13 illustrates feature extraction for multiple faces.
Figure 13:
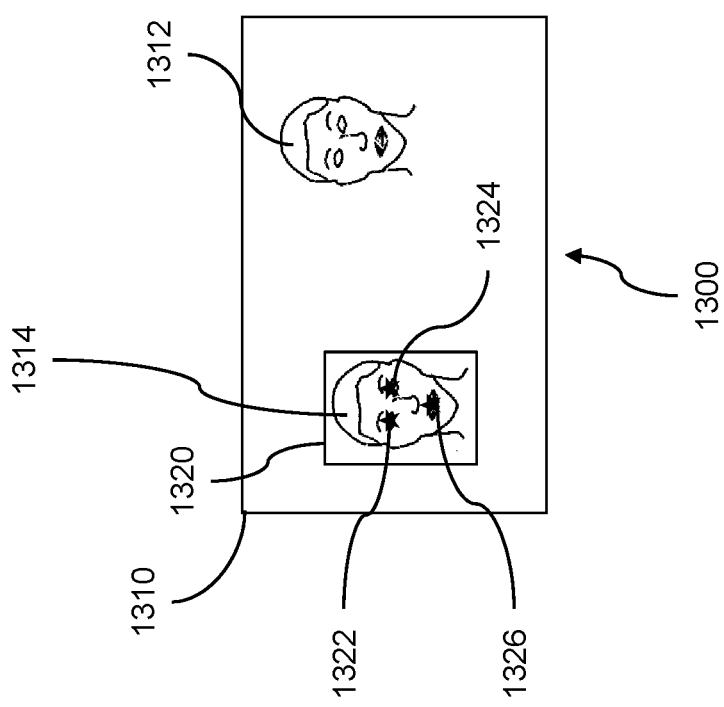

FIG. 13 illustrates feature extraction for multiple faces. Features of a face or a plurality of faces can be extracted from collected video data. Feature extraction for multiple faces can be based on sub-sectional components. The sub-sectional components can be used with performing the evaluation of content of the face. The sub-sectional components can be used to provide a context. The feature extraction can be performed by analysis using one or more processors, using one or more video collection devices, and by using a server. The analyzing device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, by analyzing a known set of data, known as a training set. The training set can include data for which category memberships of the data can be known. The training set can be used as part of a supervised training technique. If a training set is not available, then a clustering technique can be used to group observations into categories.

The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types such as numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. The classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 13, the detection of the first face, the second face, and any number of faces can include identifying facial landmarks, generating a bounding box, and prediction of a bounding box and landmarks for a next frame, where the next frame can be one of a plurality of frames of a video containing faces. A first video frame 1300 includes a frame boundary 1310, a first face 1312, and a second face 1314. The video frame 1300 also includes a bounding box 1320. Facial landmarks can be generated for the first face 1312. Face detection can be performed to initialize a second set of locations for a second set of facial landmarks for a second face within the video. Facial landmarks in the video frame 1300 can include the facial landmarks 1322, 1324, and 1326. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 1320. Bounding boxes can also be estimated for one or more other faces within the boundary 1310. The bounding box can be refined, as can one or more facial landmarks. The refining of the second set of locations for the second set of facial landmarks can be based on localized information around the second set of facial landmarks. The bounding box 1320 and the facial landmarks 1322, 1324, and 1326 can be used to estimate future locations for the second set of locations for the second set of facial landmarks in a future video frame from the first video frame.

A second video frame 1302 is also shown. The second video frame 1302 includes a frame boundary 1330, a first face 1332, and a second face 1334. Embodiments include tracking the face within the video. Furthermore, embodiments include tracking a second face within the video. The second video frame 1302 also includes a bounding box 1340 and the facial landmarks 1342, 1344, and 1346. In other embodiments, any number of facial landmarks are generated and used for facial tracking of the two or more faces of a video frame, such as the shown second video frame 1302. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either of or both the first face and the second face, and so on. Other facial points can correspond to the second face. As mentioned above, any number of facial points can be determined within a frame. One or more of the other facial points that are determined can correspond to a third face. The location of the bounding box 1340 can be estimated, where the estimating can be based on the location of the generated bounding box 1320 shown in the first video frame 1300. The three facial points shown, facial landmarks 1342, 1344, and 1346, might lie within the bounding box 1340 or might not lie partially or completely within the bounding box 1340. For instance, the second face 1334 might have moved between the first video frame 1300 and the second video frame 1302. Based on the accuracy of the estimating of the bounding box 1340, a new estimation can be determined for a third, future frame from the video, and so on. The evaluation can be performed, all or in part, on semiconductor-based logic. In embodiments, evaluation of content of the face is based on motion of regions within the face. Each video frame can be considered as an image. In embodiments, the image is one image from a series of images of the individual. Thus, in embodiments, there is a series of images. In embodiments, the series of images comprises a video of the individual.

Figure 14:
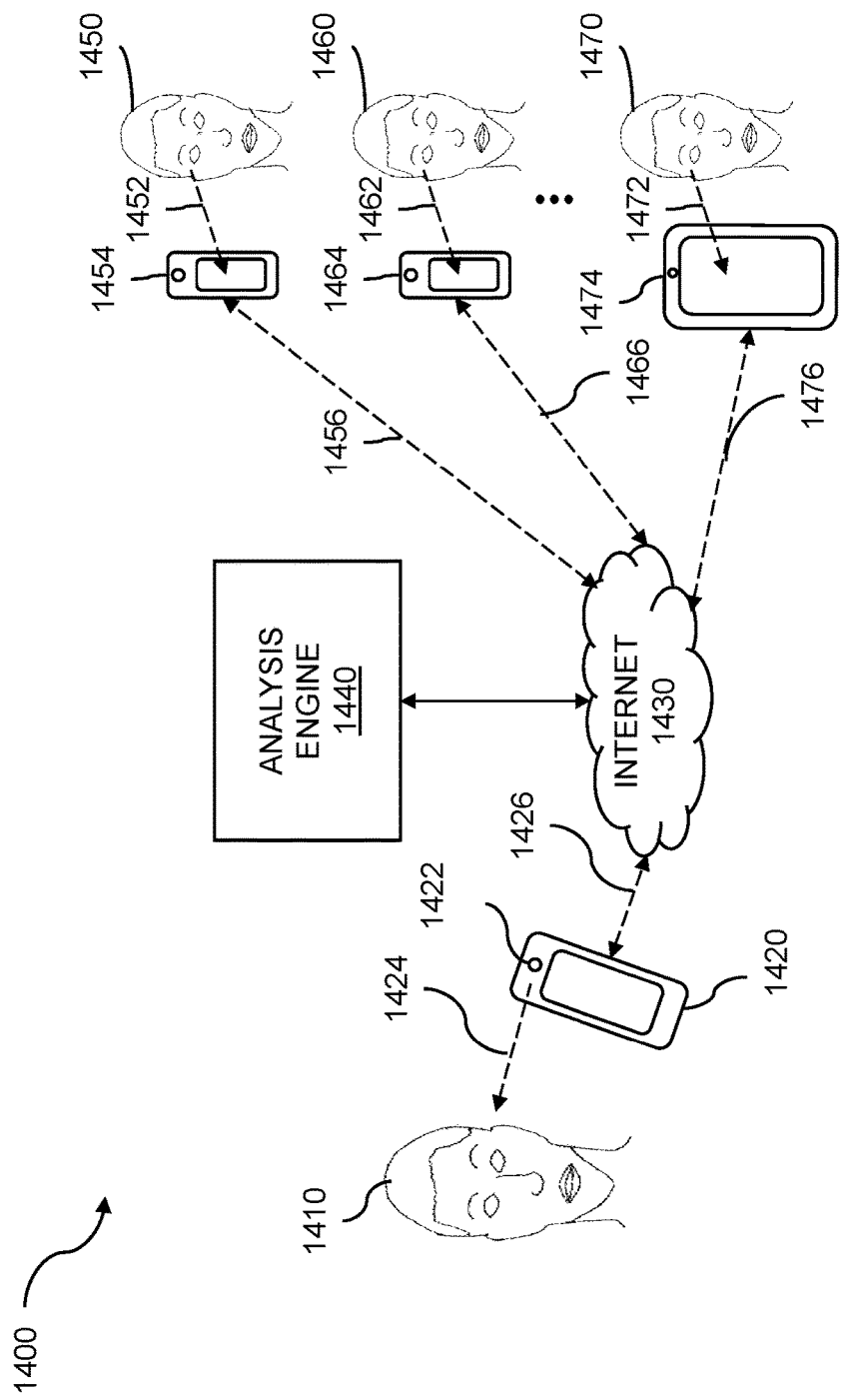
FIG. 14 shows live streaming of social video.

FIG. 14 shows live streaming of social video. A video of a person or people can be transmitted via live streaming. The live streaming of social video can be based on sub-sectional components. The sub-sectional components can be used to provide a context. The streaming and analysis can be facilitated by a video capture device, a local server, a remote server, a semiconductor-based logic, and so on. The streaming can be live streaming and can include mental state analysis, mental state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcasted spontaneously as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, "reporters" can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another live-stream video platform is Twitch™ that can be used for video streaming of video gaming and broadcasts of various competitions and events.

The example 1400 shows a user 1410 broadcasting a video live stream to one or more people as shown by the person 1450, the person 1460, and the person 1470. A portable, network-enabled electronic device 1420 can be coupled to a forward-facing camera 1422. The portable electronic device 1420 can be a smartphone, a PDA, a tablet, a laptop computer, and so on. The camera 1422 coupled to the device 1420 can have a line-of-sight view 1424 to the user 1410 and can capture video of the user 1410. The captured video can be sent to an analysis or recommendation engine 1440 using a network link 1426 to the Internet 1430. The network link can be a wireless link, a wired link, and so on. The recommendation engine 1440 can recommend to the user 1410 an app and/or platform that can be supported by the server and can be used to provide a video live-stream to one or more followers of the user 1410. In the example 1400, the user 1410 has three followers: the person 1450, the person 1460, and the person 1470. Each follower has a line-of-sight view to a video screen on a portable, networked electronic device. In other embodiments, one or more followers follow the user 1410 using any other networked electronic device, including a computer. In the example 1400, the person 1450 has a line-of-sight view 1452 to the video screen of a device 1454; the person 1460 has a line-of-sight view 1462 to the video screen of a device 1464, and the person 1470 has a line-of-sight view 1472 to the video screen of a device 1474. The portable electronic devices 1454, 1464, and 1474 can each be a smartphone, a PDA, a tablet, and so on. Each portable device can receive the video stream being broadcasted by the user 1410 through the Internet 1430 using the app and/or platform that can be suggested by the recommendation engine 1440. The device 1454 can receive a video stream using the network link 1456, the device 1464 can receive a video stream using the network link 1466, the device 1474 can receive a video stream using the network link 1476, and so on. The network link can be a wireless link, a wired link, a hybrid link, and so on. Depending on the app and/or platform that can be suggested by the recommendation engine 1440, one or more followers, such as the persons 1450, 1460, 1470, and so on, can reply to, comment on, and otherwise provide feedback to the user 1410 using their devices 1454, 1464, and 1474, respectively.

The human face provides a powerful communications medium through its ability to exhibit a myriad of expressions that can be captured and analyzed for a variety of purposes. In some cases, media producers are acutely interested in evaluating the response to and overall effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the observed person. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in levels of illumination or shadow between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made regarding the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor based logic.

Figure 15:
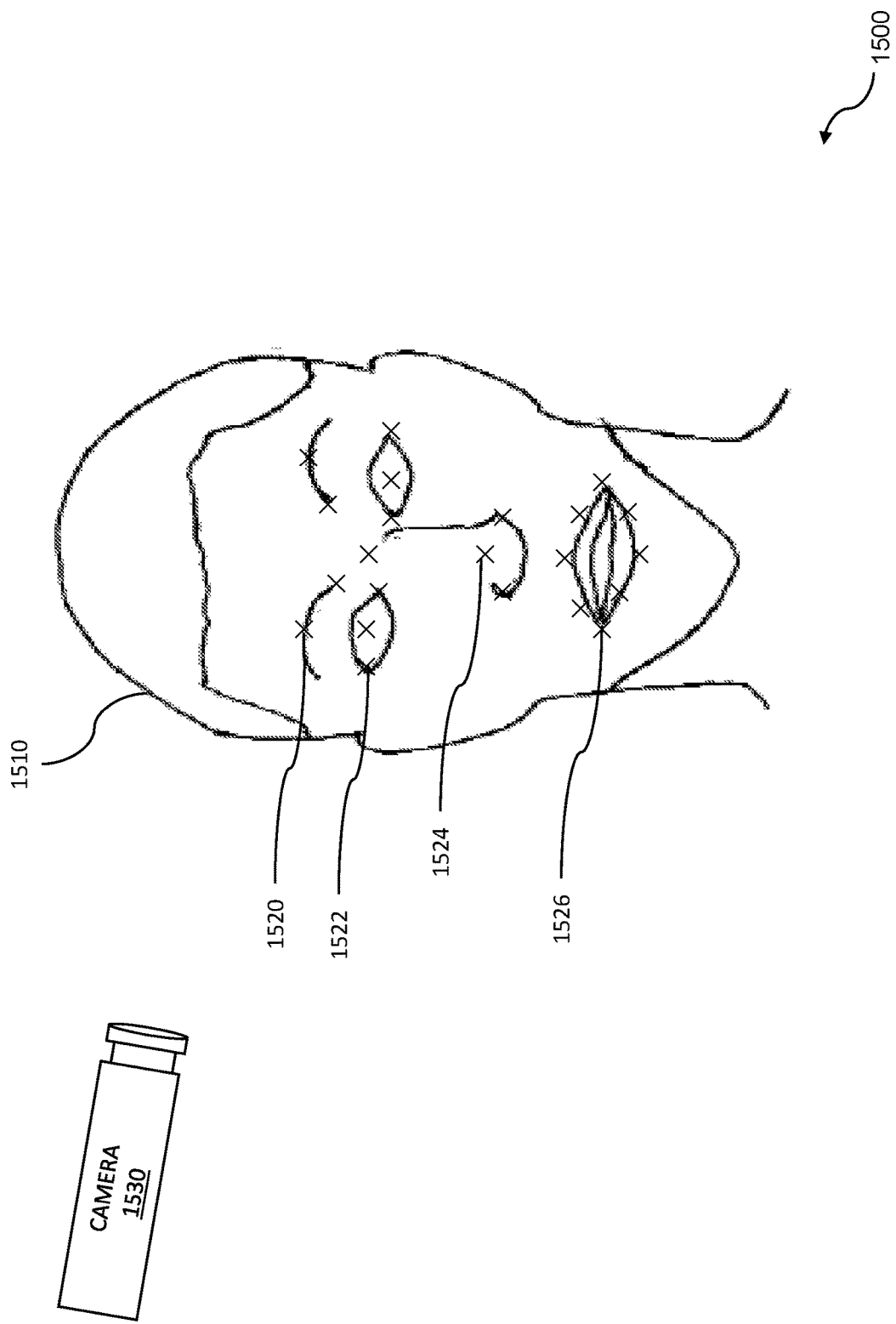
FIG. 15 shows example facial data collection including landmarks.

FIG. 15 shows example facial data collection including landmarks. In the example 1500, facial data including facial landmarks can be collected using a variety of electronic hardware and software techniques. The collecting of facial data including landmarks can be based on sub-sectional components of a population. The sub-sectional components can be used with performing the evaluation of content of the face, identifying facial landmarks, etc. The sub-sectional components can be used to provide a context. A face 1510 can be observed using a camera 1530 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person from different angles, or any other type of image capture apparatus that can allow captured data to be used in an electronic system. The quality and usefulness of the facial data that is captured can depend on the position of the camera 1530 relative to the face 1510, the number of cameras used, the illumination of the face, etc. In some cases, if the face 1510 is poorly lit or over-exposed (e.g. in an area of bright light), the processing of the facial data to identify facial landmarks might be rendered more difficult. In another example, the camera 1530 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 1520, an outer eye edge 1522, a nose 1524, a corner of a mouth 1526, and so on. Any number of facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures) with all the analysis being accomplished or augmented by a mobile device, a server, semiconductor-based logic, and so on. Thus, embodiments include performing facial landmark detection on the face of the individual.

Figure 16:
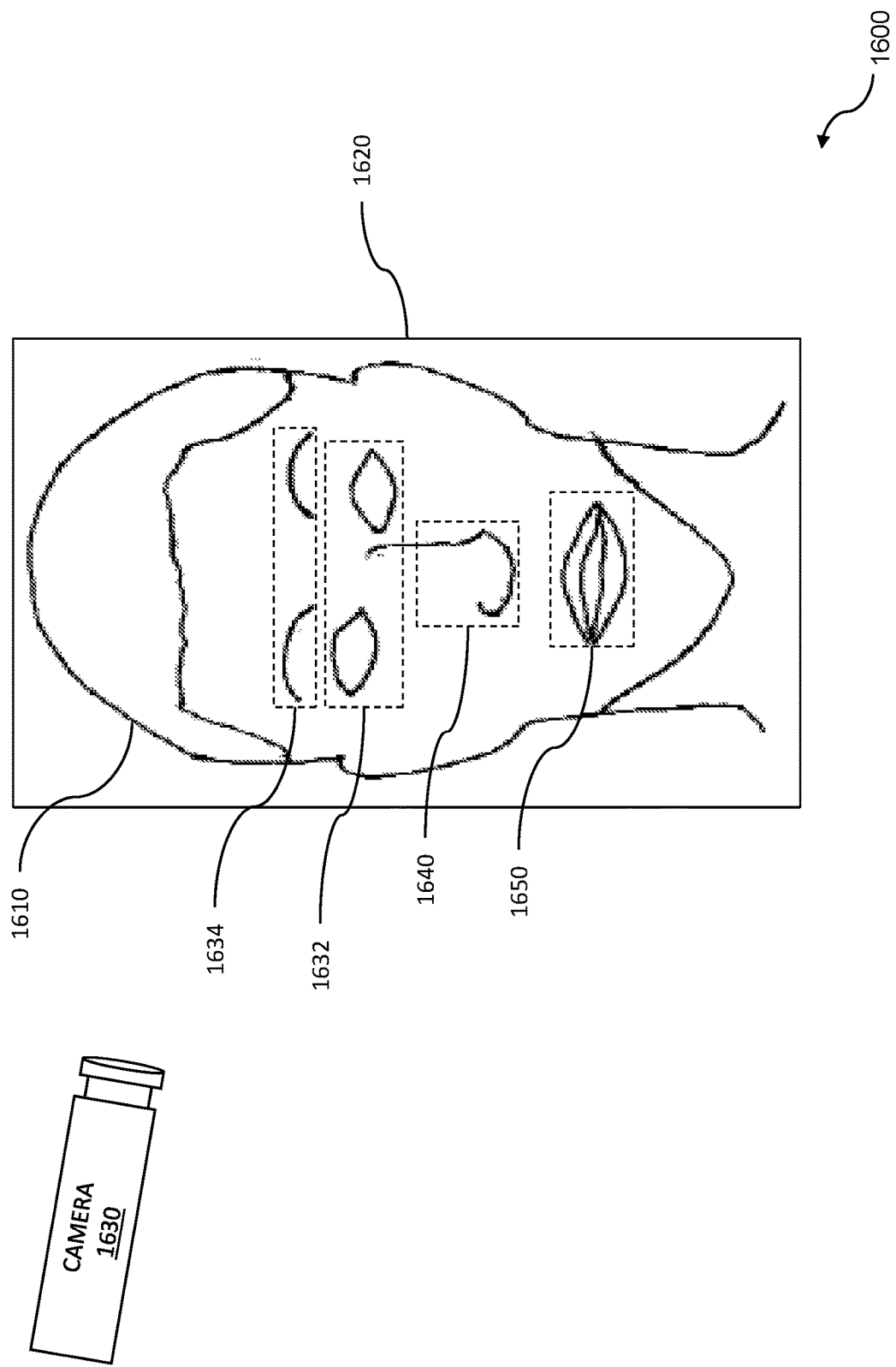
FIG. 16 shows example facial data collection including regions.

FIG. 16 shows example facial data collection including regions. Various regions of a face can be identified and used for a variety of purposes including facial recognition, facial analysis, and so on. The collecting of facial data including regions can be based on sub-sectional components of a population. The sub-sectional components can be used with performing the evaluation of content of the face, identifying facial regions, etc. The sub-sectional components can be used to provide a context. Facial analysis can be used to determine, predict, estimate, etc. mental states, emotions, and so on of a person from whom facial data can be collected. The one or more emotions that are determined by the analysis can be represented by an image, a figure, an icon, etc. The representative icon can include an emoji. One or more emoji can be used to represent a mental state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1600, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1610 can be observed using a camera 1630, a sensor, a combination of cameras and/or sensors, and so on. The camera 1630 can be used to collect facial data that can be used to determine if a face is present in an image. When a face is present in an image, a bounding box 1620 can be placed around the face. Placement of the bounding box around the face can be based on detection of facial landmarks. The camera 1630 can be used to collect from the bounding box 1620 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1630 relative to the face 1610, the number of cameras and/or sensors used, the illumination of the face, any obstructions to viewing the face, and so on.

The facial regions that can be collected by the camera 1630, sensor, or combination of cameras and/or sensors can include any of a variety of facial features. The facial features that can be included in the facial regions that are collected can include eyebrows 1634, eyes 1632, a nose 1640, a mouth 1650, ears, hair, texture, tone, and so on. Any number of facial features can be included in any number of facial regions. Thus, embodiments include extracting features within the face of the individual.

The facial regions can be analyzed to determine facial expressions including probabilities of facial expressions. In embodiments, classifiers are used for the analysis. The classifiers can include algorithms, heuristics, code segments, and so on that can be used for the analysis. For example, consider facial features that can include the eyebrows 1634. One or more classifiers can be used to analyze the facial regions that can include the eyebrows to determine a probability for either a presence or an absence of an eyebrow furrow. The presence of an eyebrow furrow can indicate the person from whom the facial data can be collected is annoyed, confused, unhappy, and so on. In another example, consider facial features can include a mouth 1650. One or more classifiers can be used to analyze the facial region that can include the mouth to determine a probability for either a presence or an absence of mouth edges turned up to form a smile. Any number of classifiers can be used to determine one or more facial expressions.

Figure 17:
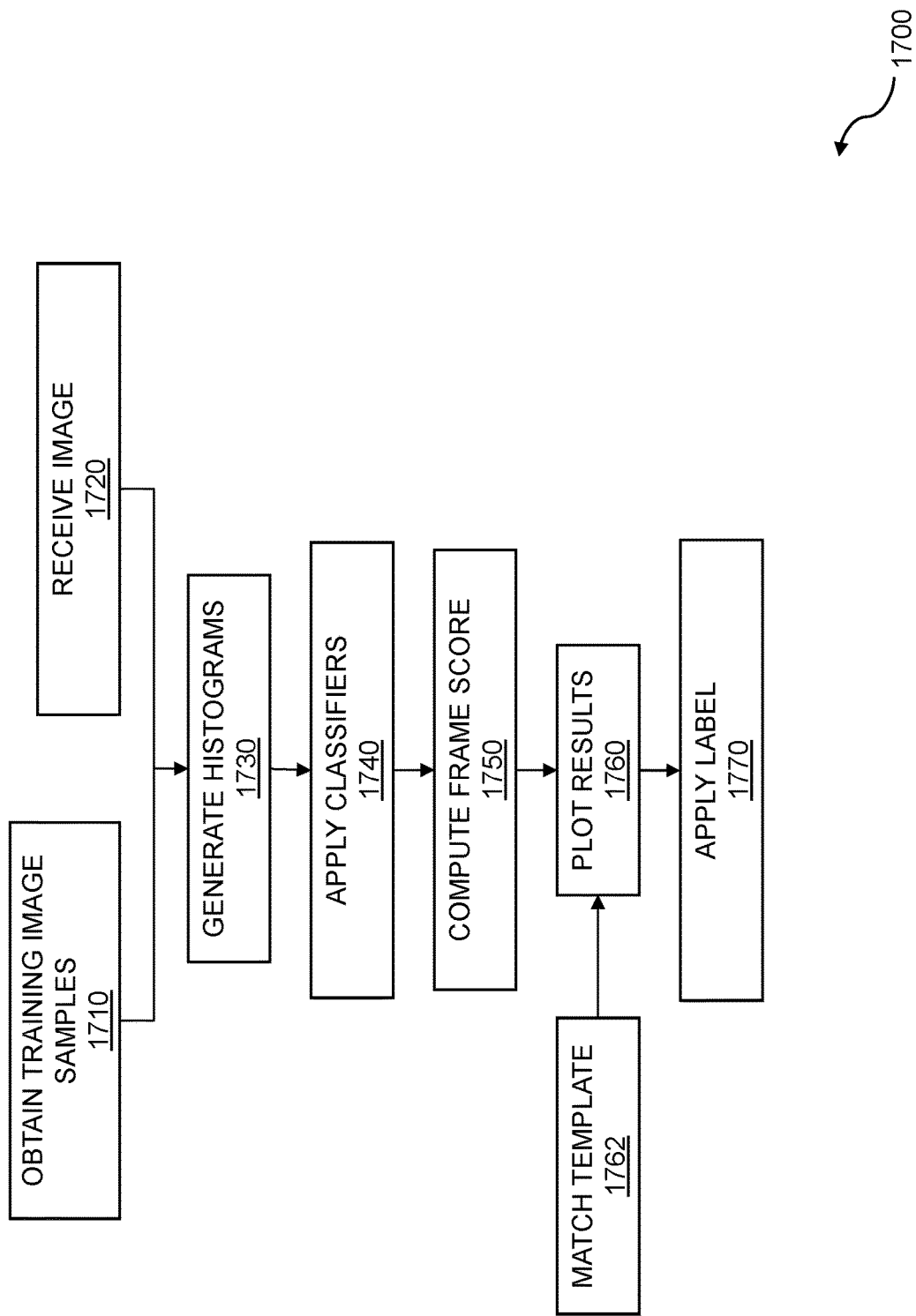
FIG. 17 is a flow diagram for detecting facial expressions.

FIG. 17 is a flow diagram for detecting facial expressions that can be used for analysis based on sub-sectional components. The sub-sectional components can be used with performing the detecting facial expressions. The sub-sectional components can be used to provide a context. The flow 1700, or portions thereof, can be implemented in semiconductor logic, can be accomplished using a mobile device, can be accomplished using a server device, and so on. The flow 1700 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk. In embodiments, image classifiers are used to map facial landmarks within the face to emotional content.

The flow 1700 begins by obtaining training image samples 1710. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1700 continues with receiving an image 1720. The image 1720 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person from different angles, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1700 continues with generating histograms 1730 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1700 continues with applying classifiers 1740 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1700 continues with computing a frame score 1750. The score computed for an image, where the image can be a frame from a video, can be used to determine the presence of a facial expression in the image or video frame. The score can be based on one or more versions of the image 1720 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1700 continues with plotting results 1760. The results that are plotted can include one or more scores for one or more frames computed over a given time t. For example, the plotted results can include classifier probability results from analysis of HoGs for a sequence of images and video frames. The plotted results can be matched with a template 1762. The template can be temporal and can be represented by a centered box function or another function. A best fit with one or more templates can be found by computing a minimum error. Other best-fit techniques can include polynomial curve fitting, geometric curve fitting, and so on. The flow 1700 continues with applying a label 1770. The label can be used to indicate that a particular facial expression has been detected in the one or more images or video frames which constitute the image that was received 1720. The label can be used to indicate that any of a range of facial expressions has been detected, including a smile, an asymmetric smile, a frown, and so on. Various steps in the flow 1700 may be changed in order, repeated, omitted, or the like without departing from the disclosed concepts. Various embodiments of the flow 1700 can be included in a computer program product embodied in a non-transitory computer readable medium that includes code executable by one or more processors. Various embodiments of the flow 1700, or portions thereof, can be included on a semiconductor chip and implemented in special purpose logic, programmable logic, and so on.

Figure 18:
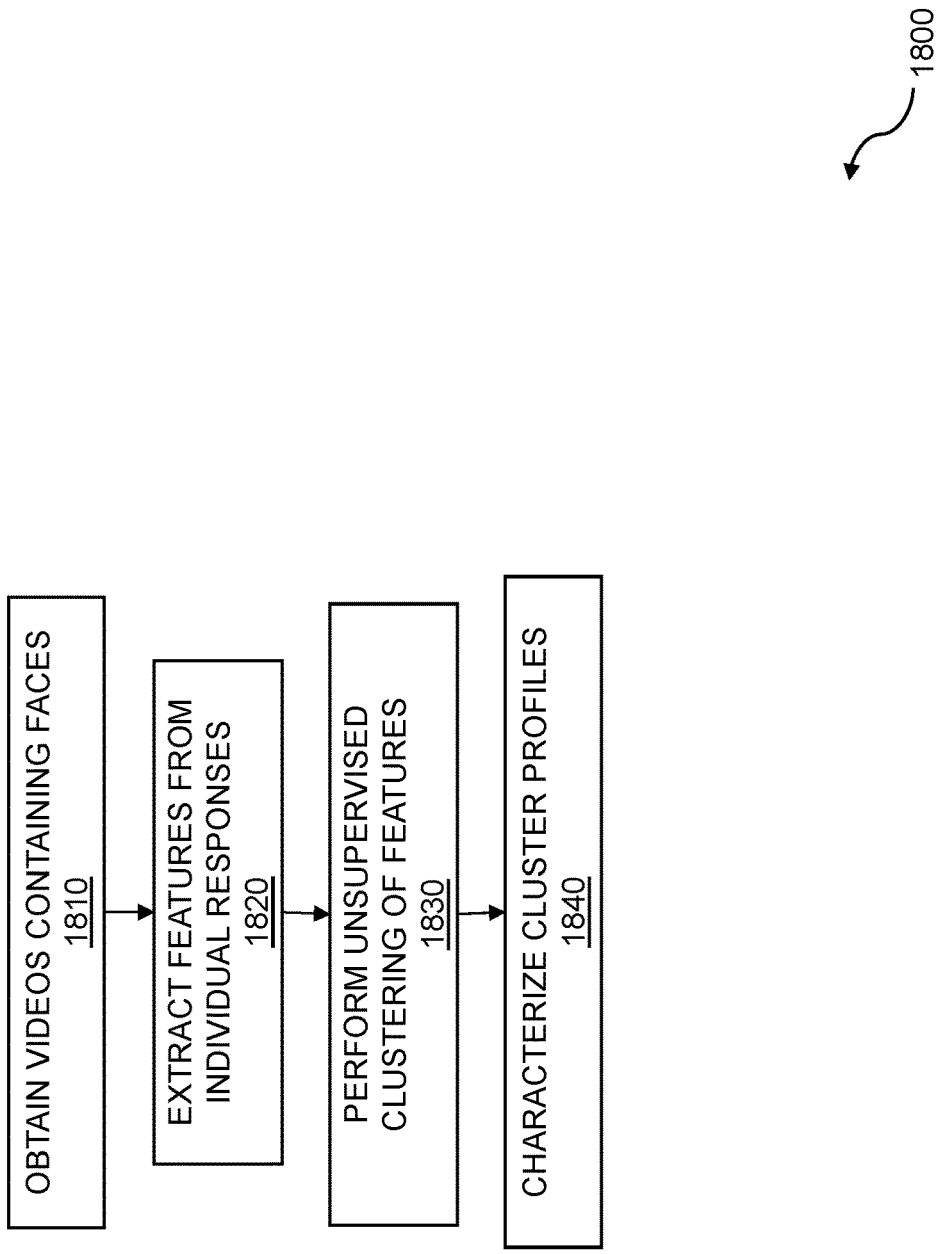
FIG. 18 is a flow diagram for the large-scale clustering of facial events.

FIG. 18 is a flow diagram for the large-scale clustering of facial events that can be used in conjunction with analysis using sub-sectional components. The sub-sectional components can be used with performing the evaluation of content of the face. The sub-sectional components can be used to provide a context. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on.

The flow 1800 begins with obtaining videos containing faces 1810. The videos can be obtained using one or more cameras, where the cameras can include a webcam coupled to one or more devices employed by the one or more people using the web-based framework. The flow 1800 continues with extracting features from the individual responses 1820. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1800 continues with performing unsupervised clustering of features 1830. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1800 continues with characterizing cluster profiles 1840. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared to various demographic groups, where the groups can be formed based on geographic location, age, ethnicity, gender, and so on.

Various steps in the flow 1800 may be changed in order, repeated, omitted, or the like without departing from the disclosed concepts. Various embodiments of the flow 1800 can be included in a computer program product embodied in a non-transitory computer readable medium that includes code executable by one or more processors. Various embodiments of the flow 1800, or portions thereof, can be included on a semiconductor chip and implemented in special purpose logic, programmable logic, and so on.

Figure 19:
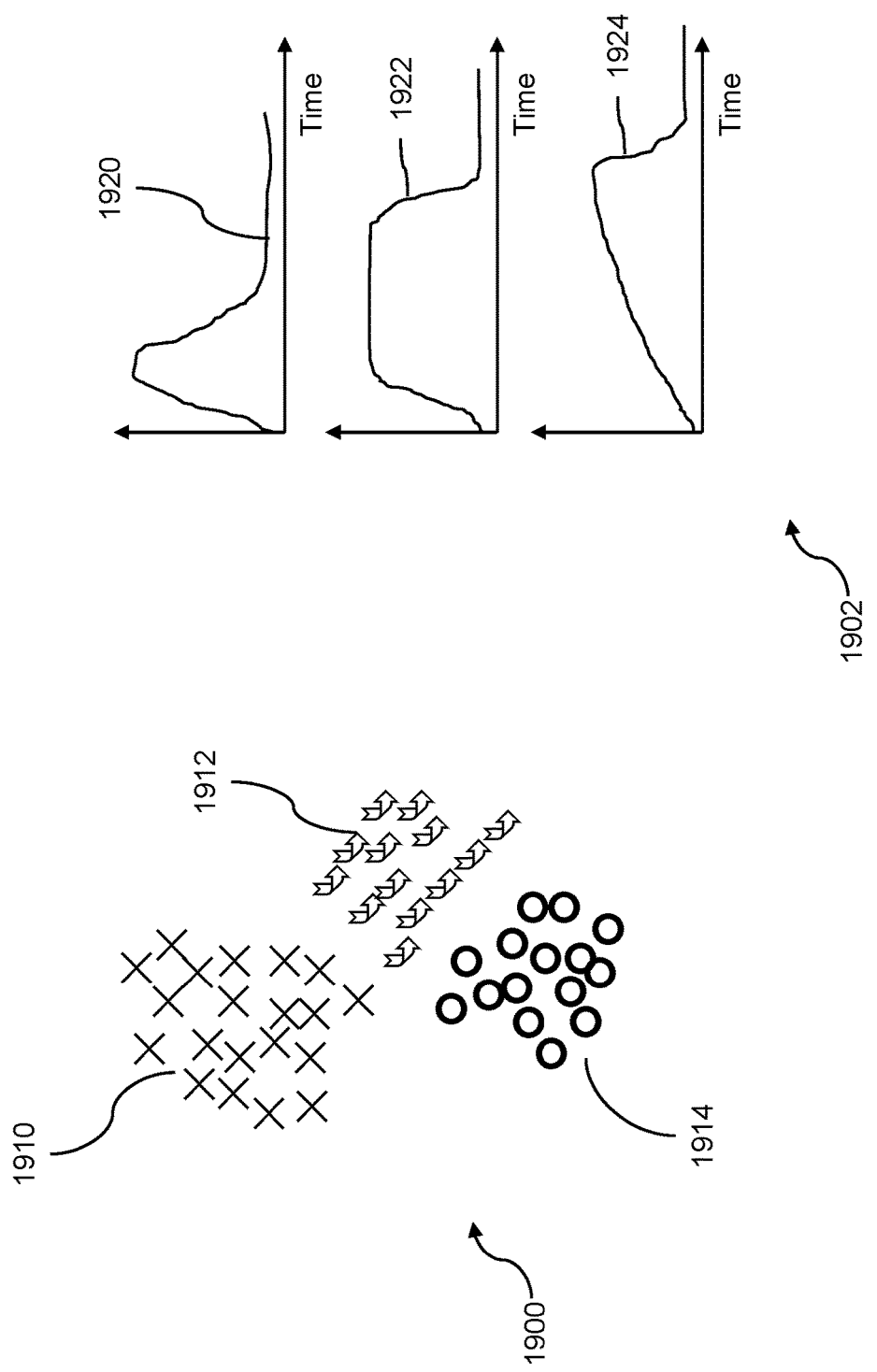
FIG. 19 shows unsupervised clustering of features and characterizations of cluster profiles.

FIG. 19 shows unsupervised clustering of features and characterizations of cluster profiles that can be used for analysis using sub-sectional components. The sub-sectional components can be used with performing the evaluation of content of the face. The sub-sectional components can be used to provide a context. Features including samples of facial data can be clustered using unsupervised clustering. Various clusters can be formed which include similar groupings of facial data observations. The example 1900 shows three clusters, clusters 1910, 1912, and 1914. The clusters can be based on video collected from people who have opted-in to video collection. When the data collected is captured using a web-based framework, the data collection can be performed on a grand scale, including hundreds, thousands, or more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information (demographic), where the demographic information can include educational level, geographic location, age, gender, income level, and so on. In embodiments, the sub-sectional component is determined based on a demographic. In embodiments, the demographic includes an age, ethnicity, culture, or gender.

The cluster profiles 1902 can be generated based on the clusters that can be formed from unsupervised clustering, with time shown on the x-axis and intensity or frequency shown on the y-axis. The cluster profiles can be based on captured facial data including facial expressions. The cluster profile 1920 can be based on the cluster 1910, the cluster profile 1922 can be based on the cluster 1912, and the cluster profile 1924 can be based on the cluster 1914. The cluster profiles 1920, 1922, and 1924 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 20A:
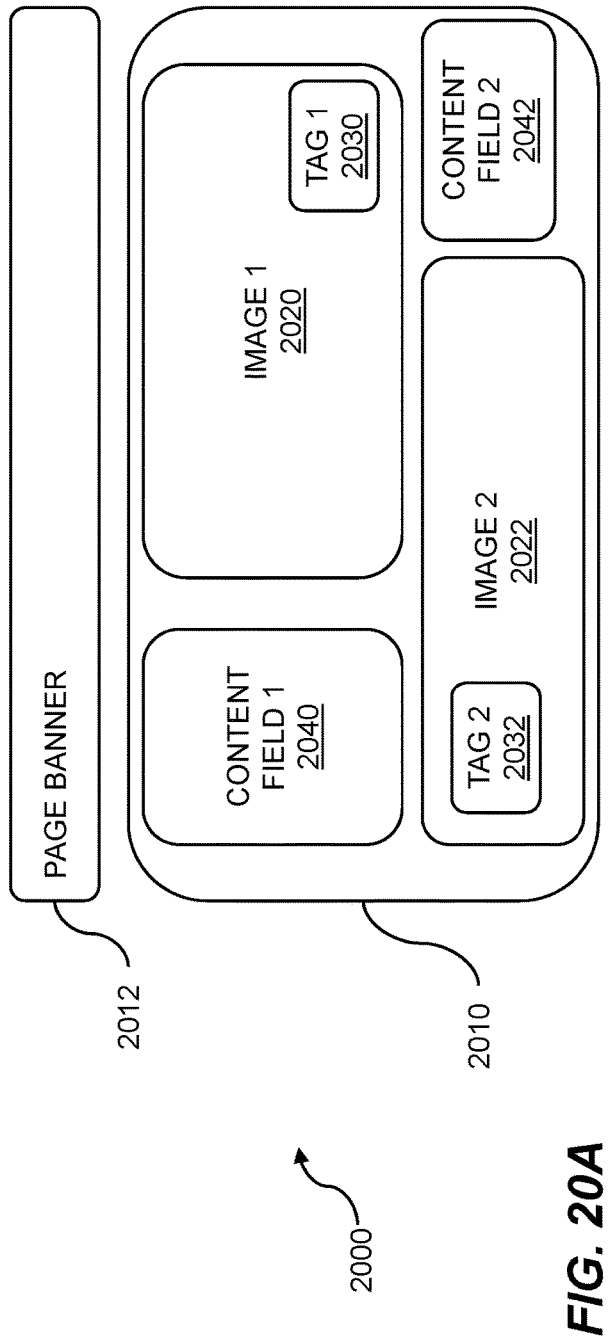
FIG. 20A shows example tags embedded in a webpage.

FIG. 20A shows example tags embedded in a webpage. The webpage can contain analysis using sub-sectional components. The sub-sectional components can be used with performing the evaluation of content of a face. The sub-sectional components can be used to provide a context. Once a tag is detected, a mobile device, a server, semiconductor based logic, etc. can be used to evaluate associated facial expressions. A webpage 2000 can include a page body 2010, a page banner 2012, and so on. The page body can include one or more objects, where the objects can include text, images, videos, audio, and so on. The example page body 2010 shown includes a first image, image 1 2020; a second image, image 2 2022; a first content field, content field 1 2040; and a second content field, content field 2 2042. In practice, the page body 2010 can contain any number of images and content fields, and can include one or more videos, one or more audio presentations, and so on. The page body can include embedded tags, such as tag 1 2030 and tag 2 2032. In the example shown, tag 1 2030 is embedded in image 1 2020, and tag 2 2032 is embedded in image 2 2022. In embodiments, any number of tags are embedded. Tags can also be embedded in content fields, in videos, in audio presentations, etc. When a user mouses over a tag or clicks on an object associated with a tag, the tag can be invoked. For example, when the user mouses over tag 1 2030, tag 1 2030 can then be invoked. Invoking tag 1 2030 can include enabling a camera coupled to a user's device and capturing one or more images of the user as the user views a media presentation (or digital experience). In a similar manner, when the user mouses over tag 2 2032, tag 2 2032 can be invoked. Invoking tag 2 2032 can also include enabling the camera and capturing images of the user. In other embodiments, other actions are taken based on invocation of the one or more tags. Invoking an embedded tag can initiate an analysis technique, post to social media, award the user a coupon or another prize, initiate mental state analysis, perform emotion analysis, and so on.

Figure 20B:
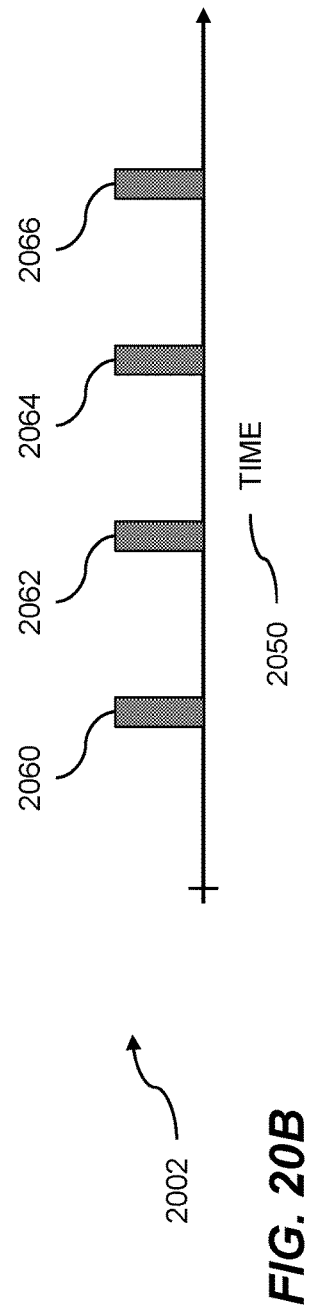
FIG. 20B shows invoking tags to collect images.

FIG. 20B shows invoking tags to collect images. The tags can be related to analysis using sub-sectional components. The sub-sectional components can be used with performing the evaluation of content of a face. The sub-sectional components can be used to provide a context. As previously stated, a media presentation can be a video, a webpage, and so on. A video 2002 can include one or more embedded tags, such as a tag 2060, another tag 2062, a third tag 2064, a fourth tag 2066, and so on. In practice, any number of tags can be included in the media presentation. The one or more tags can be invoked during the media presentation. The collection of the invoked tags can occur over time, as represented by a timeline 2050. When a tag is encountered in the media presentation, the tag can be invoked. When the tag 2060 is encountered, invoking the tag can enable a camera coupled to a user device and can capture one or more images of the user viewing the media presentation. Invoking a tag can depend on agreement to opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 2060 does not enable the camera nor capture images of the user during the media presentation. The user can indicate an opt-in for certain types of participation, where opting-in can be dependent on specific content in the media presentation. The user could opt-in to participation in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags imbedded in the media presentation that are related to advertisements would not enable the camera when invoked. Various other situations of tag invocation are possible.

Figure 21:
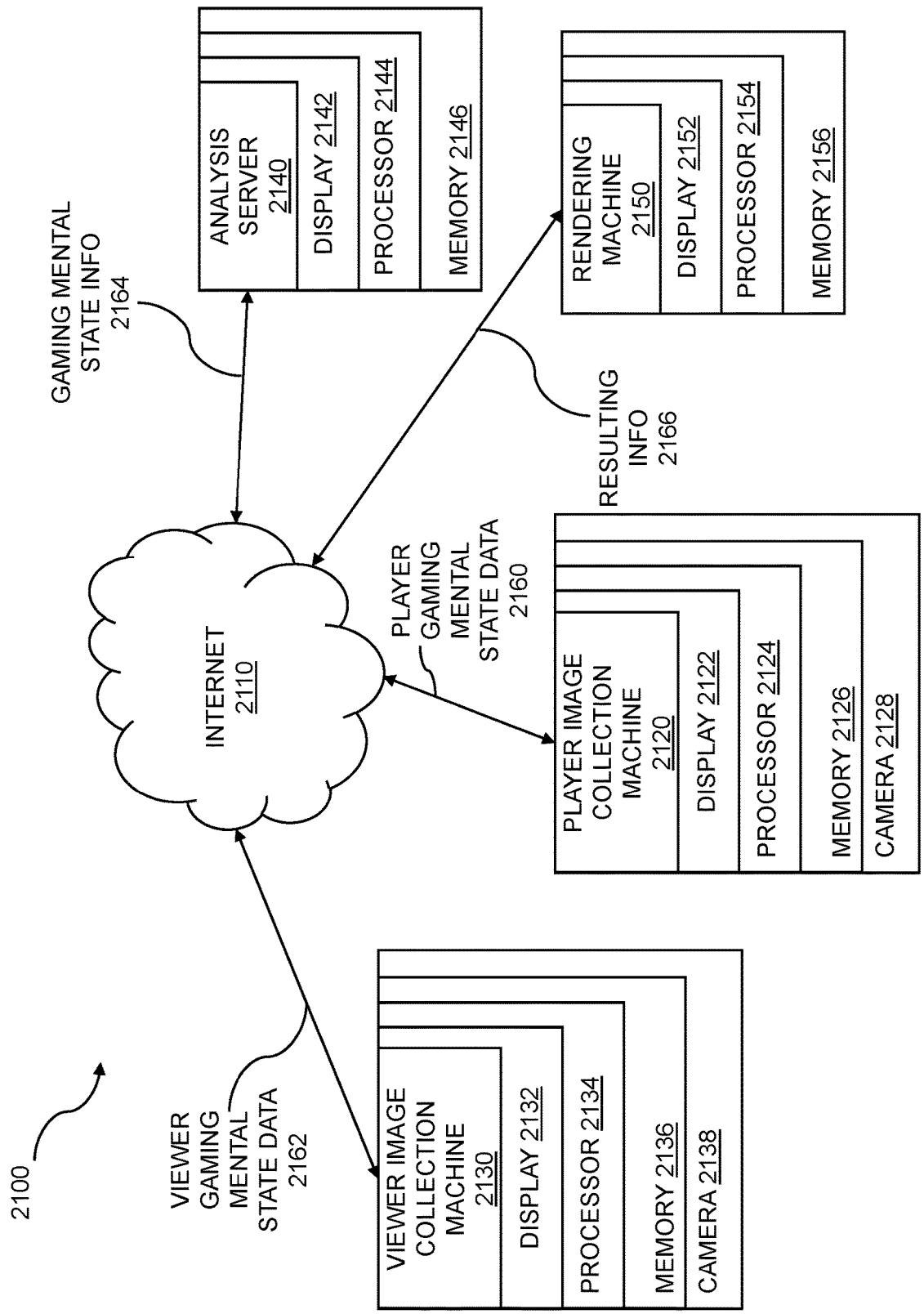
FIG. 21 is a system diagram for image analysis within a shared digital environment.

FIG. 21 is a system diagram for analytics for live streaming based on image analysis within a shared digital environment. The image analysis can include analyzing emotional content within a plurality of images for a set of participants within the plurality of participants. The results of the analyzing of the emotional content within the plurality of images can be provided to a second set of participants within the plurality of participants. The system 2100 for analytics for live streaming based on image analysis within a share digital environment can be implemented using a variety of electronic hardware and software techniques. For example, the system 2100 can be implemented using one or more machines. An example system 2100 is shown for image collection, image analysis, and rendering. The system 2100 can include a memory which stores instructions and one or more processors attached to the memory wherein the one or more processors, when executing the instructions which are stored, are configured to: obtain a plurality of images from a plurality of participants involved in an interactive digital environment; analyze emotional content within the plurality of images for a first set of participants within the plurality of participants; and provide results of the analyzing of the emotional content within the plurality of images to a second set of participants within the plurality of participants.

The system 2100 can perform a computer-implemented method for analysis comprising: obtaining a plurality of images from a plurality of participants involved in an interactive digital environment; analyzing emotional content within the plurality of images for a first set of participants within the plurality of participants; and providing results of the analyzing of the emotional content within the plurality of images to a second set of participants within the plurality of participants.

The system 2100 can include a viewer image collection machine 2130, a player image collection machine 2120, a rendering machine 2150, and an analysis server 2140. The viewer image collection machine 2130 can be configured to collect images of one or more viewers of a game within a shared digital environment and provide viewer gaming mental state data 2162 to other components within system 2100. The viewer image collection machine 2130 comprises one or more processors 2134 coupled to a memory 2136 which can store and retrieve instructions, a display 2132, and a camera 2138. The camera 2138 can include a webcam, a video camera, a still camera, a thermal imager, a CCD device, a phone camera, a three-dimensional camera, a depth camera, a light field camera, a plenoptic camera, multiple webcams used to show different views of a person from different angles, or any other type of image capture technique that can allow captured data to be used in an electronic system. The memory 2136 can be used for storing instructions, image data on a plurality of people, gaming data, one or more classifiers, one or more actions units, and so on. The display 2132 can be any electronic display, including but not limited to, a computer display, a laptop screen, a net-book screen, a tablet computer screen, a smartphone display, a mobile device display, a remote with a display, a television, a projector, or the like.

The player image collection machine 2120 can be configured to collect images of one or more players of a game within a shared digital environment and provide player gaming mental state data 2160 to other components within system 2100. The player image collection machine 2120 comprises one or more processors 2124 coupled to a memory 2126 which can store and retrieve instructions, a display 2122, and a camera 2128. The camera 2128 can include a webcam, a video camera, a still camera, a thermal imager, a CCD device, a phone camera, a three-dimensional camera, a depth camera, a light field camera, a plenoptic camera, multiple webcams used to show different views of a person from different angles, or any other type of image capture technique that can allow captured data to be used in an electronic system. The memory 2126 can be used for storing instructions, image data on a plurality of people, gaming data, one or more classifiers, one or more actions units, and so on. The display 2122 can be any electronic display, including but not limited to, a computer display, a laptop screen, a net-book screen, a tablet computer screen, a smartphone display, a mobile device display, a remote with a display, a television, a projector, or the like.

The analysis server 2140 can include one or more processors 2144 coupled to a memory 2146 which can store and retrieve instructions, and can also include a display 2142. The analysis server 2140 can receive the analytics for gaming mental state information 2164 and analyze the image data using classifiers, action units, and so on. The classifiers and action units can be stored in the analysis server, loaded into the analysis server, provided by a user of the analysis server, and so on. The analysis server 2140 can use image data received from the viewer image data collection machine 2130 and/or the player image collection machine 2120 to produce resulting information 2166. The resulting information can include emotion, mood, mental state, etc., and can be based on the analytics for live streaming. In some embodiments, the analysis server 2140 receives image data from a plurality of image data collection machines, aggregates the image data, processes the image data or the aggregated image data, and so on.

The rendering machine 2150 can include one or more processors 2154 coupled to a memory 2156 which can store and retrieve instructions and data, and can also include a display 2152. The resulting information 2166 be processed on the rendering machine 2150 or on a different platform from the rendering machine 2150. In embodiments, the rendering of the resulting information rendering data occurs on the viewer image data collection machine 2130, and/or the player image collection machine 2120, and/or on the analysis server 2140. As shown in the system 2100, the rendering machine 2150 can receive resulting information 2166 via the Internet 2110 or another network from the viewer image data collection machine 2130 and/or the player image collection machine 2120, from the analysis server 2140, or from a combination of the aforementioned machines. The rendering can include a visual display or any other appropriate display format. In some embodiments, instead of using the Internet, a private network such as a private LAN or private WAN may be used.

The system 2100 can include a computer program product embodied in a non-transitory computer readable medium for analysis, the computer program product comprising code which causes one or more processors to perform operations of: obtaining a plurality of images from a plurality of participants involved in an interactive digital environment; analyzing emotional content within the plurality of images for a first set of participants within the plurality of participants; and providing results of the analyzing of the emotional content within the plurality of images to a second set of participants within the plurality of participants.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for analysis comprising:
    obtaining a first plurality of images from a plurality of participants involved in an interactive digital environment, wherein the interactive digital environment is a shared digital environment for the plurality of participants;
    analyzing first emotional content within the first plurality of images for a first set of participants within the plurality of participants;
    modifying the interactive digital environment based on the analyzing of the first emotional content;
    analyzing second emotional content within a second plurality of images obtained from the plurality of participants to generate one or more metrics indicating whether the modifying produces effective engagement; and
    providing results of the analyzing of the second emotional content within the second plurality of images to a second set of participants within the plurality of participants, wherein the results include the one or more metrics.

2. The method of claim 1 wherein the first set of participants are players.

3. The method of claim 2 wherein the second set of participants are players.

4. The method of claim 2 wherein the second set of participants are viewers.

5. The method of claim 1 wherein the first set of participants are viewers.

6. The method of claim 5 wherein the second set of participants are players.

7. The method of claim 1 further comprising augmenting the analyzing of the first emotional content, within the first plurality of images, with evaluation of audio information.

8. The method of claim 7 wherein the audio information is collected using a microphone associated with one of the plurality of participants.

9. The method of claim 8 wherein the augmenting includes evaluating non-verbal environmental sounds in the audio information.

10. The method of claim 7 wherein the augmenting further refines analysis of the first emotional content.

11. The method of claim 7 wherein the audio information includes voice data.

12. The method of claim 1 further comprising analyzing third emotional content within the first plurality of images for the second set of participants.

13. The method of claim 12 further comprising providing an indication based on the analyzing of the third emotional content within the first plurality of images for the second set of participants to the first set of participants.

14. The method of claim 1 wherein the first set of participants substantially matches the second set of participants.

15. The method of claim 1 wherein analyzing first emotional content within the first plurality of images comprises:
    identifying an image of an individual within the plurality of participants; and
    performing an evaluation of the first emotional content based on a face for the individual by applying image classifiers to the image.

16. The method of claim 1 wherein the interactive digital environment includes a digital game.

17. The method of claim 16 wherein the interactive digital environment includes a competitive digital game.

18. The method of claim 1 further comprising analyzing spending habits of a third set of participants within the plurality of participants.

19. The method of claim 18 further comprising associating the spending habits of the third set of participants with an outcome of emotional analysis for the third set of participants.

20. The method of claim 19 further comprising modifying the interactive digital environment based on the spending habits of the third set of participants and the outcome of emotional analysis for the third set of participants.

21. The method of claim 1 wherein the plurality of participants is involved in live streaming of the interactive digital environment.

22. The method of claim 1 further comprising having a viewer, from the plurality of participants, become a player within the interactive digital environment.

23. The method of claim 22 wherein the viewer assumes a role of a player within the plurality of participants.

24. The method of claim 23 wherein the viewer receives attributes associated with the player.

25. The method of claim 23 wherein the viewer assumes the role of the player during a playback of the interactive digital environment.

26. The method of claim 1 further comprising aggregating information produced by the analyzing the first emotional content within the first plurality of images for a set of viewers within the plurality of participants.

27. The method of claim 26 further comprising presenting the information to an individual within the plurality of participants.

28. The method of claim 27 further comprising presenting an effect based on the information produced by the analyzing the first emotional content within the first plurality of images, in the interactive digital environment, for the individual to the individual.

29. The method of claim 1 wherein the modifying the interactive digital environment includes adding players to or deleting players from the interactive digital environment.

30. The method of claim 1 wherein the modifying the interactive digital environment includes adding additional game content to the interactive digital environment.

31. The method of claim 1 wherein the modifying the interactive digital environment includes changing a frequency of an event in the interactive digital environment.

32. A computer program product embodied in a non-transitory computer readable medium for analysis, the computer program product comprising code which causes one or more processors to perform operations of:
obtaining a first plurality of images from a plurality of participants involved in an interactive digital environment;
analyzing first emotional content within the first plurality of images for a first set of participants within the plurality of participants, wherein the interactive digital environment is a shared digital environment for the plurality of participants;
modifying the interactive digital environment based on the analyzing of the first emotional content;
analyzing second emotional content within a second plurality of images obtained from the plurality of participants to generate one or more metrics indicating whether the modifying produces effective engagement; and
providing results of the analyzing of the second emotional content within the second plurality of images to a second set of participants within the plurality of participants, wherein the results include the one or more metrics.

33. A computer system for analysis comprising:
a memory which stores instructions;
one or more processors attached to the memory wherein the one or more processors, when executing the instructions which are stored, are configured to:
obtain a first plurality of images from a plurality of participants involved in an interactive digital environment, wherein the interactive digital environment is a shared digital environment for the plurality of participants;
analyze first emotional content within the first plurality of images for a first set of participants within the plurality of participants;
modify the interactive digital environment based on the analysis of the first emotional content;
analyze second emotional content within a second plurality of images obtained from the plurality of participants to generate one or more metrics indicating whether the modification produces effective engagement; and
provide results of the analysis of the second emotional content within the second plurality of images to a second set of participants within the plurality of participants, wherein the results include the one or more metrics.

* * * * *